United States Patent
Watanabe

(10) Patent No.: US 12,253,450 B2
(45) Date of Patent: Mar. 18, 2025

(54) PARTICLE RECOVERY DEVICE AND PARTICLE RECOVERY METHOD

(71) Applicant: ARKRAY, Inc., Kyoto (JP)

(72) Inventor: Yukio Watanabe, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 191 days.

(21) Appl. No.: 17/812,975

(22) Filed: Jul. 15, 2022

(65) Prior Publication Data
US 2023/0072007 A1 Mar. 9, 2023

(30) Foreign Application Priority Data

Aug. 26, 2021 (JP) ................................. 2021-138414

(51) Int. Cl.
*G01N 15/02* (2024.01)
*B01D 21/00* (2006.01)
(Continued)

(52) U.S. Cl.
CPC ......... *G01N 15/02* (2013.01); *B01D 21/0087* (2013.01); *B01D 21/283* (2013.01);
(Continued)

(58) Field of Classification Search
CPC .. G01N 15/02; G01N 30/02; G01N 2030/027; G01N 15/1404; G01N 15/1459;
(Continued)

(56) References Cited

U.S. PATENT DOCUMENTS 5,902,489 A * 5/1999 Yasuda ................... B01J 19/10
96/155
6,216,538 B1 * 4/2001 Yasuda ................. G10K 15/02
73/570.5
(Continued)

FOREIGN PATENT DOCUMENTS

CN 115825047 A * 3/2023 ............. G01N 21/78
JP H10-082723 A 3/1998
(Continued)

OTHER PUBLICATIONS

The extended European search report issued by the European Patent Office on Feb. 6, 2023, which corresponds to European Patent Application No. 22191977.2-1001 and is related to U.S. Appl. No. 17/812,975.

*Primary Examiner* — Mohamed K Amara
(74) *Attorney, Agent, or Firm* — Studebaker Brackett PLLC

(57) ABSTRACT

A particle recovery device for recovering particles contained in a liquid sample, the particle recovery device comprising:
a flow cell having a flow path through which the liquid sample flows;
a density acquisition unit that acquires a density of the liquid sample;
standing wave forming means that applies an ultrasonic wave into the flow path to generate a standing wave;
a control unit that determines a frequency of the ultrasonic wave that generates the standing wave in the flow path based on the density acquired by the density acquisition
(Continued)

unit and causes the standing wave forming means to apply the ultrasonic wave of the determined frequency; and recovery means that recovers particles focused in the flow path by the standing wave.

20 Claims, 16 Drawing Sheets

(51) Int. Cl.
*B01D 21/28* (2006.01)
*C12M 1/00* (2006.01)
*C12N 13/00* (2006.01)
*G01N 30/02* (2006.01)

(52) U.S. Cl.
CPC ............ *C12M 47/02* (2013.01); *C12N 13/00* (2013.01); *G01N 30/02* (2013.01); *G01N 2030/027* (2013.01)

(58) Field of Classification Search
CPC ......... G01N 15/149; G01N 2001/4094; G01N 2015/1006; G01N 2015/1415; G01N 2015/142; G01N 1/4077; G01N 9/00; B01D 21/0087; B01D 21/283; C12M 47/02; C12N 13/00

See application file for complete search history.

(56) References Cited

U.S. PATENT DOCUMENTS

| | | | | |
|---|---|---|---|---|
| 9,421,553 | B2* | 8/2016 | Dionne | C12M 47/02 |
| 9,670,477 | B2* | 6/2017 | Lipkens | A61M 1/3678 |
| 2004/0060356 | A1* | 4/2004 | Scott | G01N 15/0255 |
| | | | | 73/865.5 |
| 2008/0181828 | A1* | 7/2008 | Kluck | B01D 17/00 |
| | | | | 422/128 |
| 2008/0217259 | A1* | 9/2008 | Siversson | B01D 21/283 |
| | | | | 210/542 |
| 2010/0006501 | A1* | 1/2010 | Laurell | A61M 1/362 |
| | | | | 210/635 |
| 2010/0323342 | A1* | 12/2010 | Gonzalez | A61B 8/48 |
| | | | | 156/219 |
| 2014/0231315 | A1* | 8/2014 | Laurell | B03B 7/00 |
| | | | | 422/527 |
| 2018/0245959 | A1* | 8/2018 | Kersey | G01F 1/206 |
| 2018/0296954 | A1* | 10/2018 | Trampler | G10K 11/04 |
| 2023/0076932 | A1* | 3/2023 | Watanabe | G01N 1/4077 |
| 2024/0043825 | A1* | 2/2024 | Bailey | C12N 13/00 |
| 2024/0100521 | A1* | 3/2024 | Evander | G10K 11/04 |

FOREIGN PATENT DOCUMENTS

| | | | | |
|---|---|---|---|---|
| JP | 2008279274 A | * | 11/2008 | ........... A61B 5/0048 |
| WO | 2013/172810 A1 | | 11/2013 | |

* cited by examiner

PARTICLE RECOVERY DEVICE AND PARTICLE RECOVERY METHOD

CROSS-REFERENCE TO RELATED APPLICATION

This application claims priority under 35 USC 119 from Japanese Patent Application No. 2021-138414, filed on Aug. 26, 2021, the disclosure of which is incorporated by reference herein.

BACKGROUND

Technical Field

The present disclosure relates to a particle recovery device and a particle recovery method.

Related Art

A flow path filled with a liquid sample containing particles is irradiated with an ultrasonic wave to form a node of a standing wave in the flow path, and particles focused on the node of the standing wave are recovered.

For example, Japanese Patent Application Laid-Open (JP-A) No. H10-82723 discloses a technique of a fine particle processing device that applies an ultrasonic wave to a flow path through which a solution containing a solvent component and a fine particle component flows to generate a node of a sound pressure of a standing wave at a predetermined position of the flow path, and thus to separate and recover the fine particle component.

In the clinical examination field, for example, a urine sediment test is performed in which the amount and type of tangible components such as red blood cells and white blood cells contained in a liquid sample such as urine are analyzed to examine a health condition of a person who has excreted urine. Since the amount of the tangible component contained in the urine is very small, it is desirable to obtain a concentrated solution in which the concentration of the tangible component in the urine is increased by recovering the tangible component contained in the urine in a small amount of solvent, and to analyze the tangible component contained in the concentrated solution.

An object of the present disclosure is to recover particles contained in a liquid sample well.

In a liquid sample such as urine, an excretion amount of urine and a component excreted from a body into urine vary depending on situations, such as water intake, sweating, and dietary restriction, and a health condition of a person who excretes urine, and therefore, the density and components of a liquid portion of urine vary. The discloser has found that a frequency of an ultrasonic wave at which a tangible component is recovered well is different depending on the density of the liquid portion of the liquid sample when the ultrasonic wave of a single frequency is applied in a flow path of a cell filled with the liquid sample such as urine to generate a standing wave having a node in the flow path, the tangible component focused on the node is recovered into a small amount of liquid to obtain a concentrated solution of the tangible component, and a recovery rate of the tangible component recovered in the concentrated solution is measured.

SUMMARY

A particle recovery device according to a first aspect of the present disclosure has been made based on the above findings, and the particle recovery device includes a flow cell having a flow path through which a liquid sample flows, a density acquisition unit that acquires a density of the liquid sample, standing wave forming means that applies an ultrasonic wave into the flow path to generate a standing wave, a control unit that determines a frequency of the ultrasonic wave that generates the standing wave in the flow path based on the density acquired by the density acquisition unit and causes the standing wave forming means to apply the ultrasonic wave of the determined frequency, and recovery means that recovers particles focused in the flow path by the standing wave.

A particle recovery device according to the first aspect of the present disclosure includes the standing wave forming means that applies the ultrasonic wave, which generates the standing wave in the flow path, into the flow path, and the control unit that determines the frequency of the ultrasonic wave based on the density of the liquid sample, thereby providing a device that recovers particles contained in the liquid sample having various densities at a high recovery rate.

A particle recovery method according to a second aspect of the present disclosure includes: acquiring a density of a liquid sample; determining a frequency of an ultrasonic wave, which generates a standing wave in a flow path through which the liquid sample flows, based on the density of the liquid sample; irradiating an inside of the flow path with the ultrasonic wave; and recovering particles, focused in the flow path, by the standing wave generated by the irradiation with the ultrasonic wave.

The particle recovery method according to the second aspect of the present disclosure provides a method of determining the frequency of the ultrasonic wave, which generates the standing wave in the flow path through which the liquid sample flows, based on the density of the liquid sample to recover the particles contained in the liquid sample having various densities and like at a high recovery rate.

According to the present disclosure, particles contained in a liquid sample having various densities and the like can be recovered well.

BRIEF DESCRIPTION OF THE DRAWINGS

Exemplary embodiments will be described in detail based on the following figures, wherein.

DETAILED DESCRIPTION

First Exemplary Embodiment (Configuration)

Figure 1:
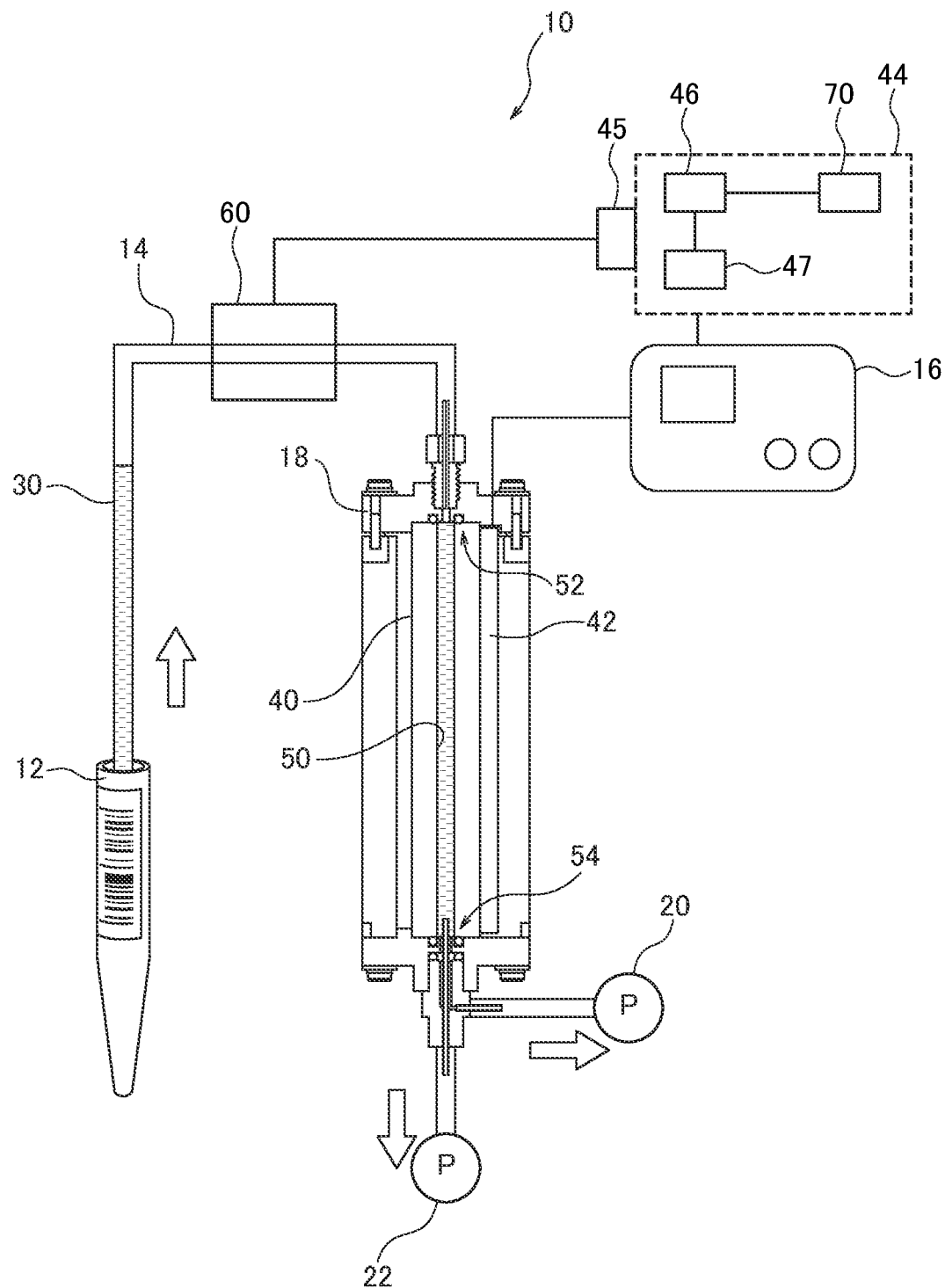
FIG. 1 is a schematic view of a configuration of a particle recovery device according to a first exemplary embodiment of the present disclosure.

First, a configuration of a particle recovery device 10 according to a first exemplary embodiment of the present disclosure will be described.

As shown in FIGS. 1 to 3 and 4A to 4C, the particle recovery device 10 according to the first exemplary embodiment of the present disclosure includes a flow cell 40, a supporting member 18 that supports the flow cell 40, a piezoelectric element 42 provided on a wall surface of the flow cell, an oscillator 16 that oscillates the piezoelectric element, a spitz tube 12 that stores a sample solution 30 (an example of a "particle-containing liquid sample" according to an exemplary embodiment of the present disclosure), an introduction path 14 that causes the sample solution 30 to flow from the spitz tube 12 into the flow cell 40, a first pump 20 and a second pump 22 that suck the sample solution 30, a control unit 44, and a density measurement unit 60 as a density acquisition unit that measures density of the sample solution 30.

As an example, the sample solution 30 is a body fluid, in particular, such as human urine containing particles such as epithelial cells, and the body fluid is recovered from a living body. The sample solution 30 flows into the flow cell 40 from a state of being stored in the spitz tube 12 through the introduction path 14.

Figure 3:
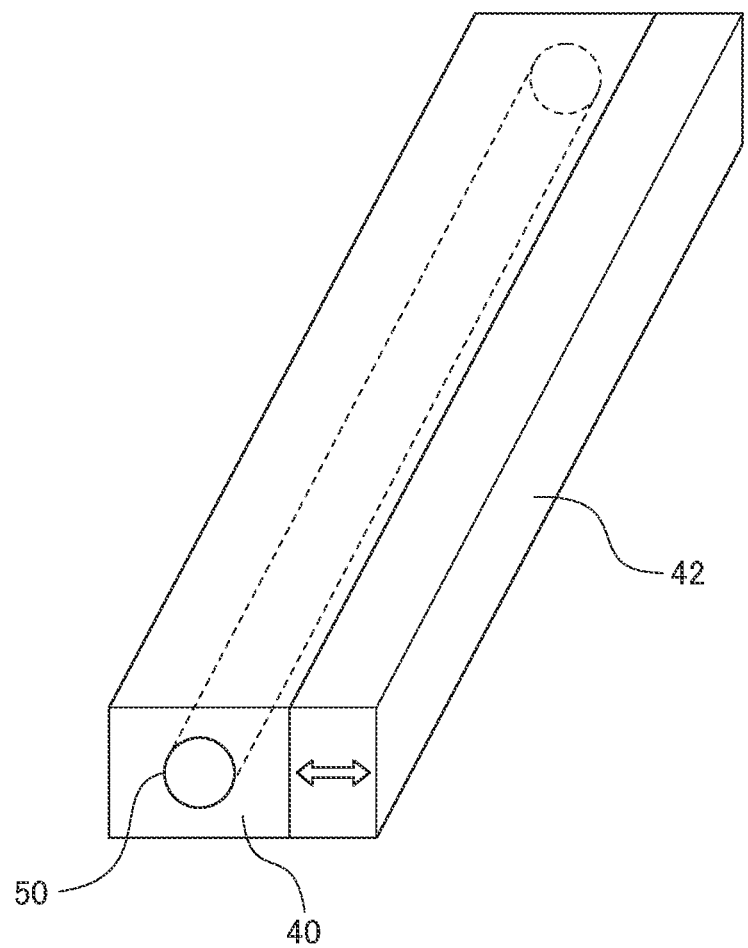
FIG. 3 is a schematic view of a flow cell according to the first exemplary embodiment of the present disclosure.

As an example, the flow cell 40 is a substantially rectangular parallelepiped member supported by the supporting member 18, and as shown in FIG. 3, a circular hole-shaped flow path 50 communicating from an upstream side to a downstream side in a longitudinal direction is formed. The piezoelectric element 42 is disposed on the wall surface of the flow cell.

The density measurement unit 60 is a device that measures the density of the sample solution 30 flowing through the introduction path 14 and flowing into the flow cell 40 or a physical property value correlated with the density (hereinafter, the density or the physical property value correlated with the density is simply referred to as "density"). Examples of the physical property value correlated with the density include the specific gravity, osmotic pressure, electric resistance value, and a refractive index of the sample solution. When the sample solution is urine, a creatinine concentration contained in the urine can be mentioned. As the density measurement unit 60, for example, a densimeter, an osmotic pressure meter, an electric resistance meter, a refractive index meter, or the like can be used.

The density measurement unit 60 is, for example, a refractive index meter provided in the introduction path 14. The refractive index meter measures a refractive index of the sample solution 30 flowing through the introduction path 14. The sample solution 30 whose refractive index has been measured flows through the flow cell provided downstream of the density measurement unit 60. The refractive index meter which is the density measurement unit 60 is connected to the control unit 44 described later, and a measurement value of the refractive index of the sample solution 30 measured by the refractive index meter is transmitted to the control unit 44.

As an example, the flow cell 40 is formed of a hard material such as glass, and is formed by cutting a central portion of a quadrangular prism block into a circular hole shape.

The upstream side of the flow path 50 is a suction port 52 into which the sample solution 30 flows from the introduction path 14 as described above, and the downstream side of the flow path 50 is a discharge port 54 that discharges the sample solution 30. In the present exemplary embodiment, a direction communicating from the suction port 52 to the discharge port 54 of the flow path 50 (direction in which the sample solution flows) is defined as a "flow direction".

Figure 2:
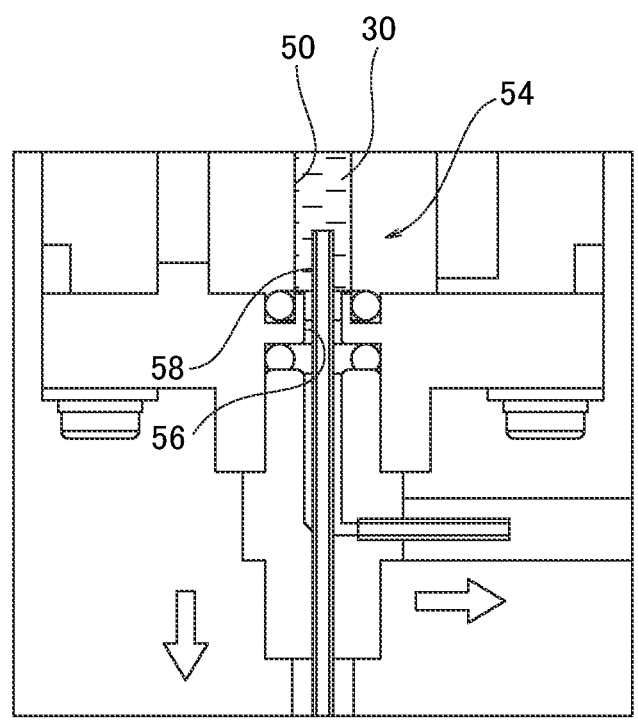
FIG. 2 is an enlarged schematic view showing a discharge port of the particle recovery device according to the first exemplary embodiment of the present disclosure.

As shown in FIG. 2, a double tube having an outer tube 56 and an inner tube 58 disposed at a center of the outer tube 56 is connected to the discharge port 54. The inner tube 58 extends from an opening of the outer tube 56 to the outside of the outer tube 56. As an example, the double tube is connected to the discharge port 54 of the flow path 50 such that the inner tube 58 is disposed along a central axis of an inner diameter of the flow path 50.

As shown in FIG. 2, the inner tube 58 is located on the downstream side (downstream side with respect to a portion where a standing wave SW to be described later is generated) of a portion of the flow path 50 with which the piezoelectric element 42 is in contact, on the central axis of the flow path 50, and is opened toward the upstream side.

Here, the outer tube 56 is bent in an L shape and is connected to the first pump 20. The inner tube 58 is connected to the second pump 22. Thus, by driving the first pump 20 and the second pump 22, the sample solution 30 stored in the spitz tube 12 can be sucked to the flow cell 40 and caused to flow into the flow cell 40, and the sample solution 30 in the flow path 50 can be separately discharged to the outside through the outer tube 56 and the inner tube 58.

The particles in the sample solution 30 are discharged to the outside through the inner tube 58 and then recovered. That is, the first pump 20, the second pump 22, the outer tube 56, and the inner tube 58 constitute "recovery means" according to an exemplary embodiment of the present disclosure.

It is desirable that the first pump 20 and the second pump 22 can be driven independently, and the sample solution 30 can be sucked from the spitz tube 12 to the flow cell 40 by driving only the first pump 20.

As shown in FIG. 2, an inner diameter of the outer tube 56 is substantially the same as an inner diameter of the flow path 50, and an inner diameter of the inner tube 58 is equal to or less than about half of the inner diameter of the flow path 50. That is, a cross-sectional area of an inside of the inner tube 58 is equal to or less than about ¼ of a cross-sectional area of an inside of the outer tube 56. A diameter of the inner tube 58 is smaller than a wavelength of an ultrasonic wave generated by the piezoelectric element 42.

The piezoelectric element 42 is a member that expands and contracts in a predetermined direction when an alternating-current voltage is supplied, and is provided in a state of being in contact with one side surface of the flow cell 40 along the flow direction of the flow cell 40.

The oscillator 16 supplies the alternating-current voltage to the piezoelectric element 42 of the flow cell 40 described above, thereby expanding and contracting the piezoelectric element 42 in a thickness direction (direction toward an inner wall surface of the flow cell 40). As a result, the ultrasonic wave, which is a compressional wave directed toward the inside of the flow cell 40 from the side surface of the flow cell 40 to which the piezoelectric element 42 is attached, is transmitted to the inner wall surface of the flow cell 40, that is, the inside of the flow path 50. When the generated ultrasonic wave is transmitted to the flow path 50, the sample solution 30 stored in the flow path 50 is irradiated with the ultrasonic wave.

Figure 4C:
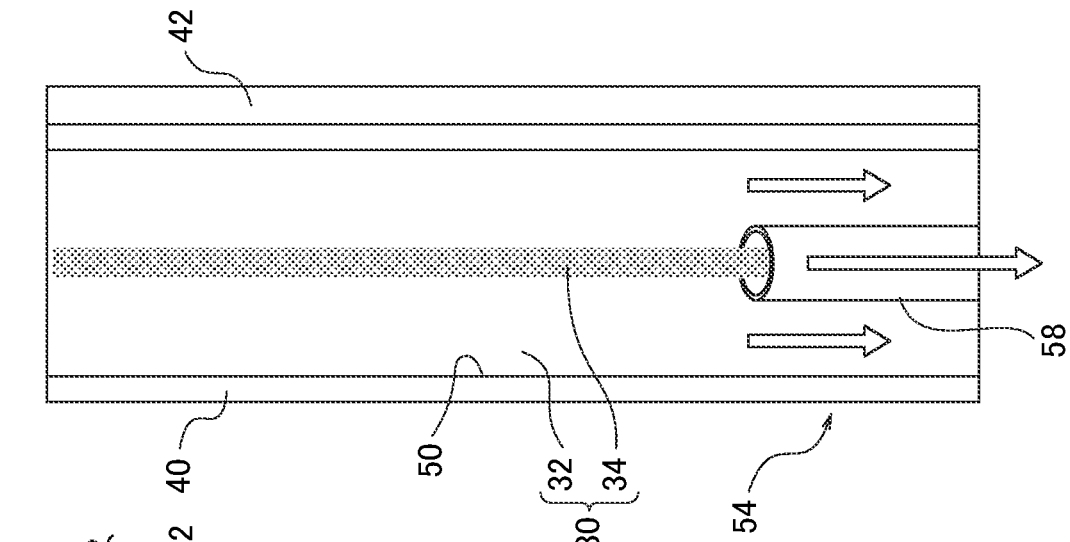
FIGS. 4A to 4C are schematic views of particle recovery by the particle recovery device according to the first exemplary embodiment of the present disclosure.
Figure 4B:
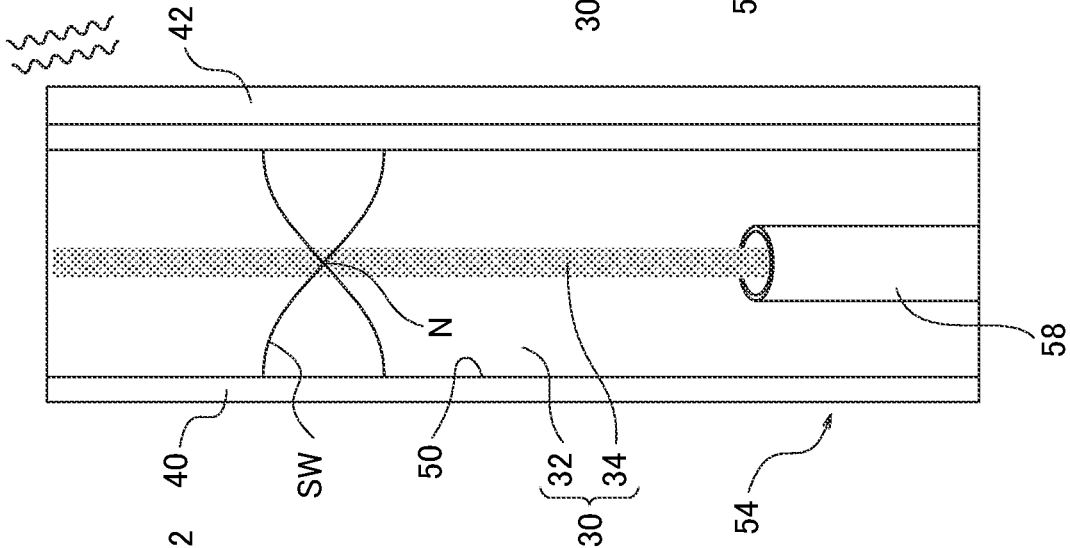
Figure 4A:
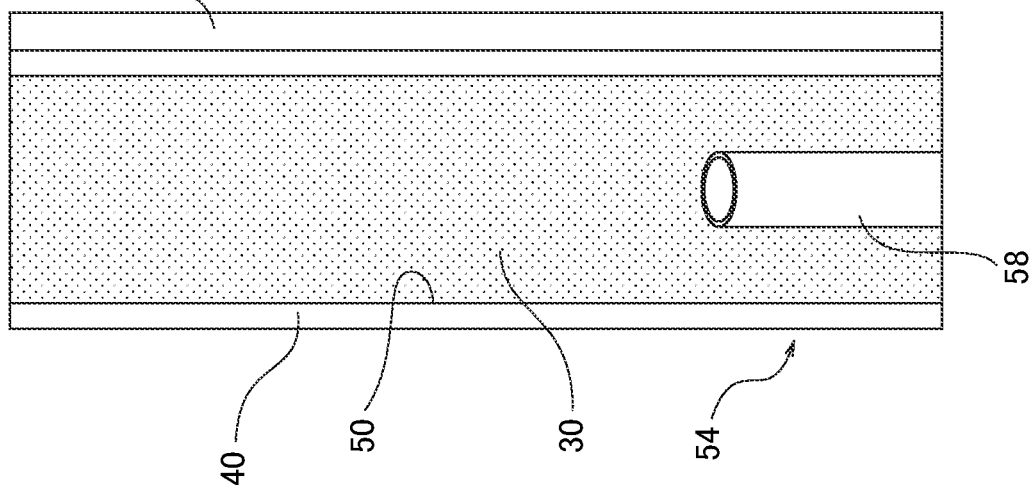

Here, as shown in FIGS. 4A to 4C, in an inner wall surface of the flow path 50, the wall surface on a side on which the piezoelectric element 42 is provided is defined as an inner wall surface A, and the wall surface on an opposite side of the inner wall surface A across the central axis is defined as an inner wall surface B.

As described above, since the ultrasonic wave emitted from the piezoelectric element 42 is transmitted to the flow path 50 through the wall surface of the flow cell 40, the sample solution 30 is irradiated with the ultrasonic wave (ultrasonic wave A) from the inner wall surface A side in the flow path 50. The piezoelectric element 42, the inner wall surface A, and the oscillator 16 correspond to a first ultrasonic irradiation unit that irradiates the sample solution 30 with the ultrasonic wave.

Then, the ultrasonic wave (ultrasonic wave A) transmitted to the sample solution 30 reaches the inner wall surface B side on an opposite side across an axial center of the flow path 50.

At this time, a part of the ultrasonic wave (ultrasonic wave A) having reached the inner wall surface B is not transmitted through the inner wall surface B but reflected by the inner wall surface B. That is, a part of the ultrasonic wave having reached the inner wall surface B travels through the sample solution 30 again toward the inner wall surface A side. That is, the piezoelectric element 42, the inner wall surface B, and the oscillator 16 correspond to a second ultrasonic irradiation unit that irradiates the ultrasonic wave B having the same frequency and amplitude as those of the ultrasonic wave A but having the opposite traveling direction and overlapping with the ultrasonic wave A. The second ultrasonic irradiation unit faces the first ultrasonic irradiation unit.

A part of the ultrasonic wave B having reached the inner wall surface A again is additionally not transmitted through the inner wall surface A and is reflected by the inner wall surface A. That is, a part of the ultrasonic wave having reached the inner wall surface A travels through the sample solution 30 toward the inner wall surface B side again.

Since the piezoelectric element 42 continuously generates the ultrasonic wave (ultrasonic wave A), the inside of the above-described flow path 50 is continuously irradiated with the ultrasonic wave.

At this time, when the wavelengths of the ultrasonic wave A and the ultrasonic wave B satisfy the condition described in the following expression (1), the ultrasonic waves reflected on the inner wall surface A side and the inner wall surface B side overlap and are amplified, so that the standing wave SW is generated in a direction orthogonal to the flow direction inside the flow path 50. L is an inner diameter [m] of the flow path 50, λ is a wavelength [m] of the ultrasonic wave, and n is an arbitrary integer of 1 or more.

[Math. 1]

$$L \approx \tfrac{1}{2}\lambda n \tag{1}$$

That is, the oscillator 16, the piezoelectric element 42, the inner wall surface A, and the inner wall surface B are an example of a "standing wave forming means" according to an exemplary embodiment of the present disclosure.

The frequency of the alternating-current voltage supplied from the oscillator 16 is equal to the frequency of the ultrasonic wave emitted from the piezoelectric element 42 to the sample solution 30 in the flow path 50. That is, the frequency of the ultrasonic wave emitted from the piezoelectric element 42 can be changed by changing the frequency of the alternating-current voltage supplied from the oscillator 16 to the piezoelectric element 42.

In addition, a voltage value (amplitude) of the alternating-current voltage supplied from the oscillator 16 and the amplitude of the ultrasonic wave emitted from the piezoelectric element 42 have a correspondence relationship, and it is possible to modulate the amplitude of the ultrasonic wave emitted from the piezoelectric element 42 by modulating the voltage value (amplitude) of the alternating-current voltage supplied from the oscillator 16 to the piezoelectric element 42.

Here, in the oscillator 16, the frequency and amplitude of the alternating-current voltage supplied to the piezoelectric element 42 are controlled by a waveform controller 46 included in the control unit 44 to be described later.

The control unit 44 includes, for example, a storage unit 70, a waveform controller 46, a reception unit 45 that receives a density value from the density measurement unit 60, and a waveform derivation unit 47. The reception unit 45 receives the density value of the sample solution 30 from the density measurement unit 60. That is, the control unit 44 and the density measurement unit 60 are an example of a density acquisition unit that acquires the density of the sample solution 30. The waveform derivation unit 47 determines the frequency and amplitude of the alternating-current voltage supplied to the piezoelectric element 42 by the oscillator 16 based on the density value of the sample solution 30 received by the reception unit 45 and a correspondence relationship between the density of the sample solution 30 and the frequency stored in the storage unit 70. Then, the waveform controller 46 controls the oscillator 16 so that the frequency and amplitude of the alternating-current voltage determined by the waveform derivation unit 47 are supplied to the piezoelectric element 42.

The configuration of the reception unit 45 is not particularly limited, and the receiving unit may be connected to the density measurement unit 60 in a wired manner to receive the density value of the sample solution 30 from the density measurement unit 60, or may be connected to the density measurement unit 60 in a wireless manner to receive the density value of the sample solution 30 from the density measurement unit 60. The control unit 44 may instruct the density measurement unit 60 to transmit the density value to the reception unit 45, and the density measurement unit 60 may transmit the density value to the reception unit 45 according to the instruction from the control unit 44.

The density measurement unit 60 may actively transmit the density value to the reception unit 45. Similarly, examples of the waveform controller 46 and the waveform derivation unit 47 include an arithmetic device and a control device such as a microcontroller and a microprocessor.

(Generation of Standing Wave and Concentration Principle of Particles)

As shown in FIG. 4A, in a state before the flow path 50 is filled with the sample solution 30 and irradiated with the ultrasonic wave, the particles contained in the sample solution 30 are uniformly dispersed in the sample solution 30.

When the alternating-current voltage is supplied to the piezoelectric element 42 in this state and the ultrasonic wave is emitted from the piezoelectric element 42, the ultrasonic wave is applied into the sample solution 30 in the flow path 50 along the wall surface of the flow cell 40.

Here, when a wavelength λ of the ultrasonic wave propagating through the sample solution 30 has a length of about ½ with respect to the diameter of the flow path 50, that is, when n=1 in the expression (1) described above, the standing wave SW is generated in the sample solution 30 in a radial direction of the flow path 50 as shown in FIG. 4B. The inner wall surface A and the inner wall surface B are free ends of the standing wave.

In this case, as shown in FIG. 4B, a node N of the standing wave SW is generated on the central axis of the flow path 50, and an antinode AN of the standing wave SW is generated on the inner wall surface of the flow path 50, that is, the inner wall surface A and the inner wall surface B. Then, the particles dispersed between the antinode AN and the node N of the standing wave SW move toward a position of the node N of the standing wave SW. As a result, the particles in the sample solution 30 are focused at the position of the node N of the standing wave SW, and at a portion other than the node N of the standing wave SW, the particles in the sample solution 30 are reduced, that is, the concentration is reduced; therefore, a portion (concentrated solution) 34 where the particles are focused and a portion (low-concentration liquid) 32 where the particles are hardly contained are generated in the sample solution 30. In other words, the density of the particles in the sample solution 30 is biased depending on the position in the flow path 50, the concentration (density) of the particles is high at a position where the node N of the standing wave SW is present, and the concentration (density) of the particles is low at a position other than the position where the node N is present.

Here, even when vibration of the piezoelectric element 42 is stopped from the state shown in FIG. 4B, the particles are not immediately dispersed in the entire sample solution 30 and remain at the position where the node N of the standing wave SW has been present for a while. Thus, a state in which the sample solution 30 is divided into the concentrated solution 34 and the low-concentration liquid 32 is maintained inside the flow cell 40. That is, the concentration (density) of the particles is high at the position where the node N of the standing wave SW has been present, and the concentration (density) of the particles is low at the position other than the position where the node N has been present.

Then, as shown in FIG. 4C, when the first pump 20 and the second pump 22 are each driven in a state where the concentration (density) of the particles of the sample solution 30 at the position where the node N of the standing wave SW is present is high, the particles focused at the position of the node N are discharged to the inner tube 58 provided downstream as the concentrated solution 34, and the low-concentration liquid 32 is discharged to the outer tube 56.

As described above, the piezoelectric element 42 is vibrated so as to generate the standing wave SW in the radial direction of the flow path 50 with respect to the sample solution 30, and the liquid in which the particles are focused is recovered from the inner tube 58, so that the particles can be concentrated.

As shown in FIG. 4C, when the particles are discharged by the first pump 20 and the second pump 22 after the particles in the sample solution 30 are focused, it is preferable to discharge the particles in a state where the flow of the sample solution 30 is a laminar flow inside the flow path 50 in order to prevent the particles from being discharged from the outer tube 56 due to disturbance of the liquid flow. The sample solution 30 may be recovered in a state of being irradiated with the ultrasonic wave.

A discharge amount of the first pump 20 connected to the outer tube 56 is larger than a discharge amount of the second pump 22 connected to the inner tube 58. A ratio of the discharge amounts in the first pump 20 and the second pump 22 according to an exemplary embodiment of the present disclosure is desirably equal to a ratio of a cross-sectional areas of the diameters of the outer tube 56 and the inner tube 58.

(Determination of First Frequency)

In the particle recovery device according to the present exemplary embodiment, an example of a procedure for determining an optimal frequency which is the frequency of the ultrasonic wave capable of recovering the particles in the sample solution 30 well will be described as a procedure for measuring the sample solutions 30 of Samples 1 to 5. For each sample, the same human urine was used as a matrix as a standard component.

As the sample solution 30 of Sample 1, human epithelial cells which were tangible components in urine were added as particles to urine prepared by mixing a plurality of urine of healthy persons for averaging. The density of the sample solution 30 of Sample 1 was 1.01 g/cm$^3$.

As the sample solution 30 of Sample 2, glucose was added to Sample 1 to adjust the density to 1.02 g/cm$^3$.

As the sample solution 30 of Sample 3, urea was added to Sample 1 to adjust the density to 1.02 g/cm$^3$.

As the sample solution 30 of Sample 4, albumin was added to Sample 1 to adjust the density to 1.02 g/cm$^3$.

As the sample solution 30 of Sample 5, glucose was added to Sample 1 to adjust the density to 1.05 g/cm$^3$.

As the sample solution 30 of Sample 6, urea was added to Sample 1 to adjust the density to 1.05 g/cm$^3$.

As the sample solution 30 of Sample 7, albumin was added to Sample 1 to adjust the density to 1.05 g/cm$^3$.

Table 1 below summarizes the description of Samples 1 to 7 above.

TABLE 1

| Sample No. | Tangible component | Density (g/cm³) | Type of sample solution |
|---|---|---|---|
| Sample 1 | Epithelial cell | 1.01 | Urine |
| Sample 2 | Epithelial cell | 1.02 | Urine added with glucose |
| Sample 3 | Epithelial cell | 1.02 | Urine added with urea |
| Sample 4 | Epithelial cell | 1.02 | Urine added with albumin |
| Sample 5 | Epithelial cell | 1.05 | Urine added with glucose |
| Sample 6 | Epithelial cell | 1.05 | Urine added with urea |
| Sample 7 | Epithelial cell | 1.05 | Urine added with albumin |

For the sample solutions 30 of Samples 1 to 7, the concentration of the tangible component contained in the concentrated solution 34 after undergoing the following concentration treatment procedure was compared with the concentration of the tangible component of the sample solution 30 before performing the concentration treatment procedure, and a concentration ratio was calculated. In addition, the concentration ratio was multiplied by a ratio between the flow rate of the concentrated solution 34 and the flow rate of the sample solution 30 to obtain a recovery rate. The recovery rate indicates a ratio (B/A) of the number (B) of the tangible components contained in the concentrated solution 34 to the number (A) of the tangible components contained in the sample solution 30 before performing the concentration treatment procedure. In the present exemplary embodiment, since the flow rate of the concentrated solution 34 is 20% of the flow rate of the sample solution 30, it can be said that the concentration is performed when the recovery rate exceeds 20%. When the recovery rate exceeds 20%, it can be said that the standing wave SW having a node formed at the center of the flow path 50 is generated.

Figure 5:
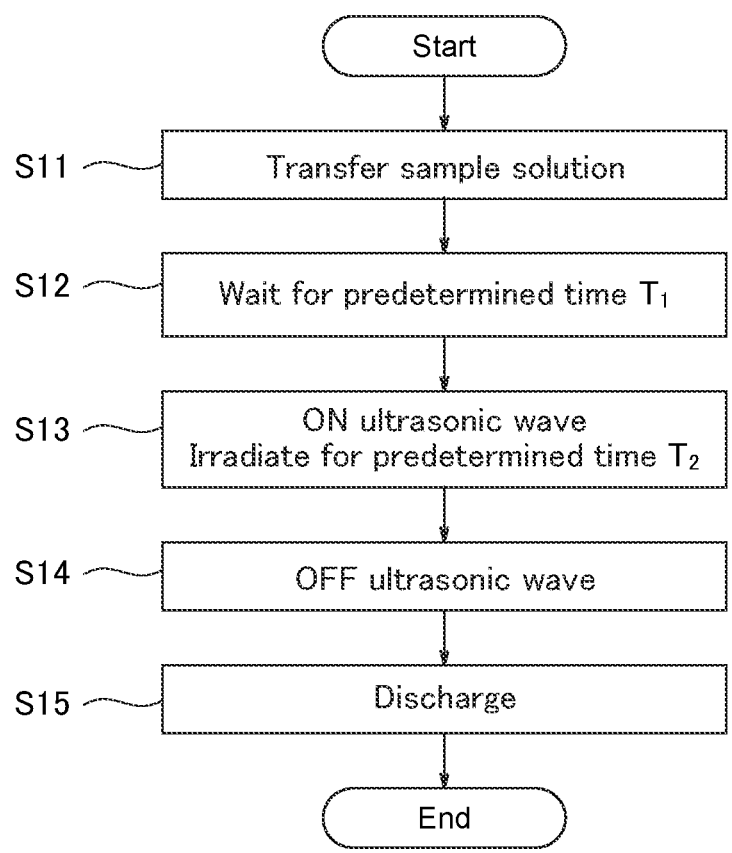
FIG. 5 is a flowchart of an optimal frequency measurement procedure by the particle recovery device according to the first exemplary embodiment of the present disclosure.

FIG. 5 is a flowchart of an operation procedure of the particle recovery device for measuring the frequency of the ultrasonic wave where the standing wave SW is generated.

First, as a first step S11, only the first pump 20 is driven in a state where the second pump 22 is stopped, whereby the sample solution 30 stored in the spitz tube 12 is caused to flow into the flow path 50 in the flow cell 40.

Next, in a second step S12, after the sample solution 30 is caused to flow into the flow path 50, the first pump 20 is stopped, and waiting is performed for a predetermined time T1 until the flow of the sample solution 30 in the flow path 50 does not flow.

Next, as a third step S13, the piezoelectric element 42 is vibrated by supplying the alternating-current voltage of 60 V constant voltage from the oscillator 16 to the piezoelectric element 42, and the sample solution 30 in the flow path 50 is irradiated with an ultrasonic wave of a constant frequency for a predetermined time T2, so that the node N is generated on the central axis with respect to the flow cell 40.

Next, as a fourth step S14, the supply of the alternating-current voltage from the oscillator 16 to the piezoelectric element 42 is stopped, and the vibration of the piezoelectric element 42 is stopped.

Next, as a fifth step S15, the first pump 20 and the second pump 22 are driven to cause the concentrated solution 34 to flow out to the inner tube 58 and the low-concentration liquid 32 to flow out to the outer tube 56 as shown in FIG. 4(C), thereby discharging the sample solution 30 from the flow path 50.

Here, in the third step S13, Sample 1 was irradiated with ultrasonic waves having frequencies of 330 kHz, 330.5 kHz, and 331 kHz, Samples 2 to 4 were irradiated with ultrasonic waves having frequencies of 330.5 kHz, 331 kHz, and 331.5 kHz, Samples 5 and 7 were irradiated with ultrasonic waves having frequencies of 332.5 kHz, 333 kHz, and 333.5 kHz, and Sample 6 was irradiated with ultrasonic waves having frequencies of 332.5 kHz, 333 kHz, 333.5 kHz, 334 kHz, and 334.5 kHz.

Figure 6A:
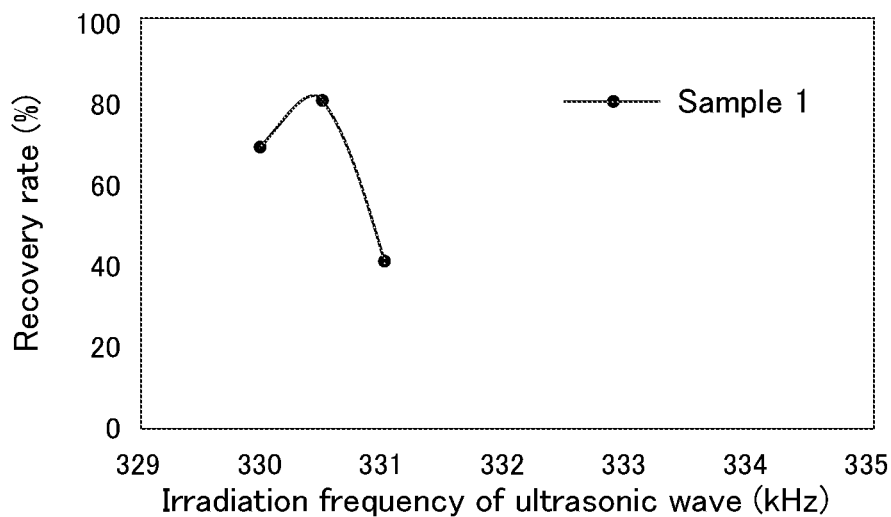
FIGS. 6A to 6C are graphs showing a change in a recovery rate obtained by the optimal frequency measurement procedure using the particle recovery device according to the first exemplary embodiment of the present disclosure.
Figure 6B:
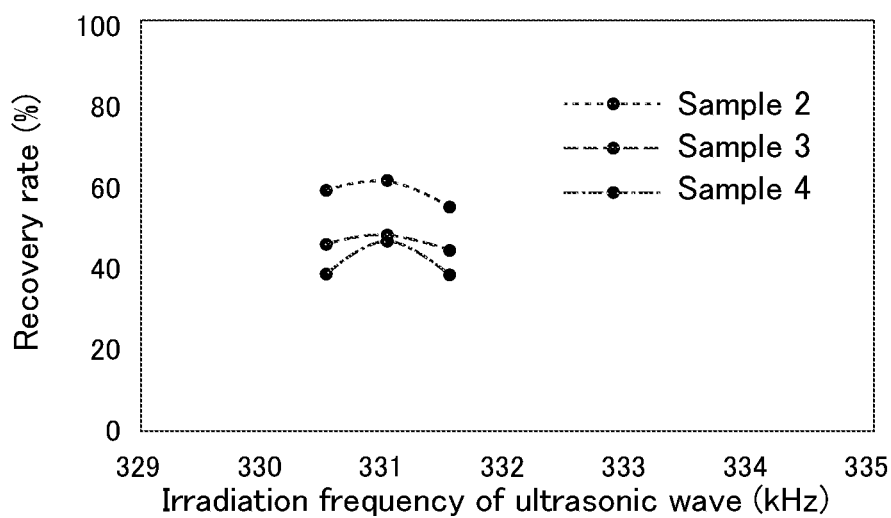
Figure 6C:
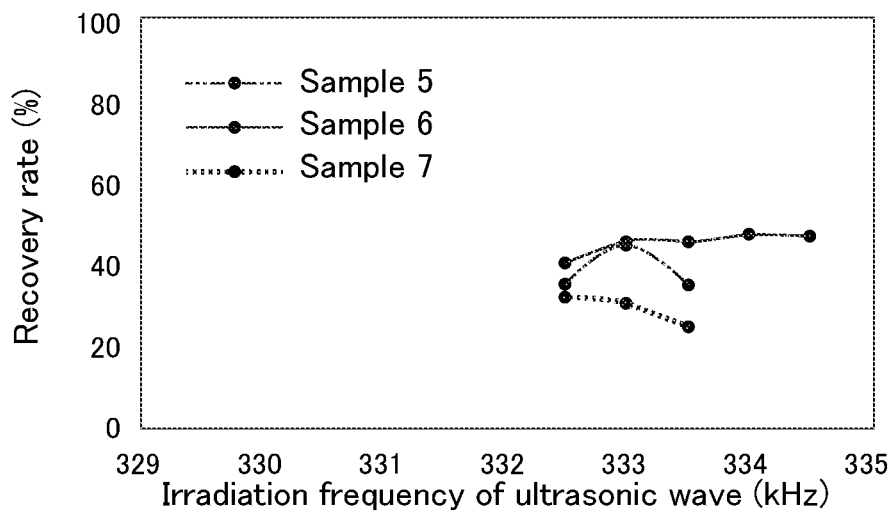

FIGS. 6A to 6C show the results of measuring the recovery rate by performing the concentration treatment described above on the sample solutions 30 of Samples 1 to 7 and measuring and comparing the concentration of the tangible component before and after the concentration treatment.

As shown in FIG. 6A, in the sample solution 30 of Sample 1 having a density of 1.01 g/cm³, the recovery rate exceeded 20% at frequencies of 330 kHz, 330.5 kHz, and 331 kHz, and therefore it can be said that the standing wave SW was generated. The recovery rate was most improved when the frequency of the ultrasonic wave to be applied was set to 330.5 kHz. It was estimated that the recovery rate was low when the ultrasonic wave having a frequency of 331 kHz or more was applied. As described above, by irradiating the sample solution 30 of Sample 1 with the ultrasonic wave having a frequency of 330.5 kHz, the particles in the sample solution 30 were efficiently recovered.

Similarly, as shown in FIG. 6B, in the sample solutions 30 of Samples 2, 3, and 4 having a density of 1.02 g/cm³, the recovery rate exceeded 20% at frequencies of 330.5 kHz, 331 kHz, and 331.5 kHz, and therefore it can be said that the standing wave SW was generated. The recovery rate was most improved when the frequency of the ultrasonic wave to be applied was set to 331 kHz. As described above, by irradiating the sample solutions 30 of Samples 2, 3, and 4 with the ultrasonic wave having a frequency of 331 kHz higher than 330.5 kHz at which the highest recovery rate was obtained in Sample 1, the particles in the sample solution 30 can be efficiently recovered.

Similarly, as shown in FIG. 6C, in the sample solutions 30 of Samples 5 and 7 having a density of 1.05 g/cm³, the recovery rate exceeded 20% at frequencies of 332.5 kHz, 333 kHz, and 333.5 kHz, and therefore it can be said that the standing wave SW was generated. In the sample solution 30 of Sample 6 having a density of 1.05 g/cm³, the recovery rate exceeded 20% at frequencies of 332.5 kHz or more and 334.5 kHz or less, and therefore it can be said that the standing wave SW was generated. The recovery rate was most improved when the frequency of the ultrasonic wave to be applied was set to 333 kHz in Sample 5, 334 kHz in Sample 6, and 332.5 kHz in Sample 7. As described above, by irradiating the sample solutions of Samples 5, 6, and 7 with the ultrasonic waves respectively having frequencies of 333 kHz, 334 kHz, and 332.5 kHz higher than 331 kHz at which the highest recovery rate was obtained in Samples 2 to 4, the particles in the sample solution 30 were efficiently recovered.

From this, it can be seen that it is possible to generate the standing wave SW and set the frequency of the ultrasonic wave at which the recovery rate is improved for any of the sample solutions 30 of Samples 1 to 7 by the concentration treatment described above. In Samples 1 to 7, since the density is different for each sample, it is found that the frequency of the ultrasonic wave at which the particles in the sample solution 30 can be efficiently recovered is different. The frequency at which particles of a sample having a high density are recovered well tended to be higher than the frequency at which particles of a sample having a low density are recovered well. From this, it is found that the density of the sample and the frequency at which the particles of the sample are recovered well have a correlation, and the particles contained in the sample are recovered well by irradiating the sample with the ultrasonic wave having a frequency corresponding to the density of the sample.

Therefore, as in Samples 1 to 7, when the sample solutions 30 having different densities are irradiated with the ultrasonic waves at frequencies corresponding to the respective densities, the standing wave SW can be generated even when the densities of the sample solutions 30 are different.

Thus, a first frequency at which the tangible component contained in the sample representing the sample solution 30 of each density is recovered well is obtained. The first frequency is the frequency of the ultrasonic wave at which the standing wave SW is generated on the central axis of the flow path 50 containing the sample solution 30 and the particles in the sample solution 30 are efficiently recovered. Then, a "density versus frequency relationship" described later, which is a correspondence relationship between the density and the first frequency, is obtained, and the "density versus frequency relationship" is stored in the storage unit 70.

Then, a second frequency is derived from the density measurement value obtained by measuring the density of the sample solution 30 and the density versus frequency relationship. It is presumed that the second frequency is the frequency at which the particles contained in the sample solution 30 are recovered well. Then, the frequency of the ultrasonic wave with which the sample solution in the flow path according to the first exemplary embodiment is irradiated is determined.

As the first frequency, for example, a plurality of the sample solutions 30 having the same density are provided, the frequencies at which the tangible components contained in the sample solution 30 are recovered at a high recovery rate are obtained, and a median or an average value of the obtained frequencies can be taken as the first frequency. Moreover, the plurality of sample solutions 30 are mixed to prepare an averaged sample solution, and the frequency at which the tangible components contained in the averaged sample solution are recovered well can be taken as the first frequency.

When the frequency of the ultrasonic wave is f[Hz], f can be obtained by the following expression (2). v is a sound velocity [m/s] traveling in the sample solution 30.

[Math. 2]
$$f = \frac{v}{\lambda} \quad (2)$$

Then, by substituting the expression (1) into the expression (2) and deforming the expression, the following expression (3) is obtained.

[Math. 3]
$$n \approx 2f\frac{L}{v} \quad (3)$$

Here, in the expression (3) described above, n can take an arbitrary integer value (n=1, 2, 3, . . . ) as a so-called vibration mode. That is, if the frequency f of the ultrasonic wave is set to a frequency at which n is an integer value, the standing wave SW can be generated in the flow path 50.

A number of the nodes N in the standing wave SW is an integer value having the same value as n. For example, when the frequency f of the ultrasonic wave is set such that n is 2, the number of the nodes N of the generated standing wave SW is 2.

As the position where the node N is generated, the node N is generated at a position obtained by equally dividing a distance from the inner wall surface A to the inner wall surface B (radial length of the flow path 50) by n+1. For example, when n=1, the node N is generated at a position of ½ with respect to the length from the inner wall surface A to the inner wall surface B. When n=2, the node N is generated at positions of ⅓ and ⅔ with respect to the length from the inner wall surface A to the inner wall surface B.

In this way, when n=1, the position of the node N of the standing wave SW in the particle recovery device 10 according to the present exemplary embodiment is only on the central axis of the flow path 50 as in the state shown in FIG. 4(B).

(Procedure of Particle Concentration Treatment)

Subsequently, a particle concentration method according to the first exemplary embodiment of the present disclosure will be described with appropriate reference to FIG. 7.

Figure 7:
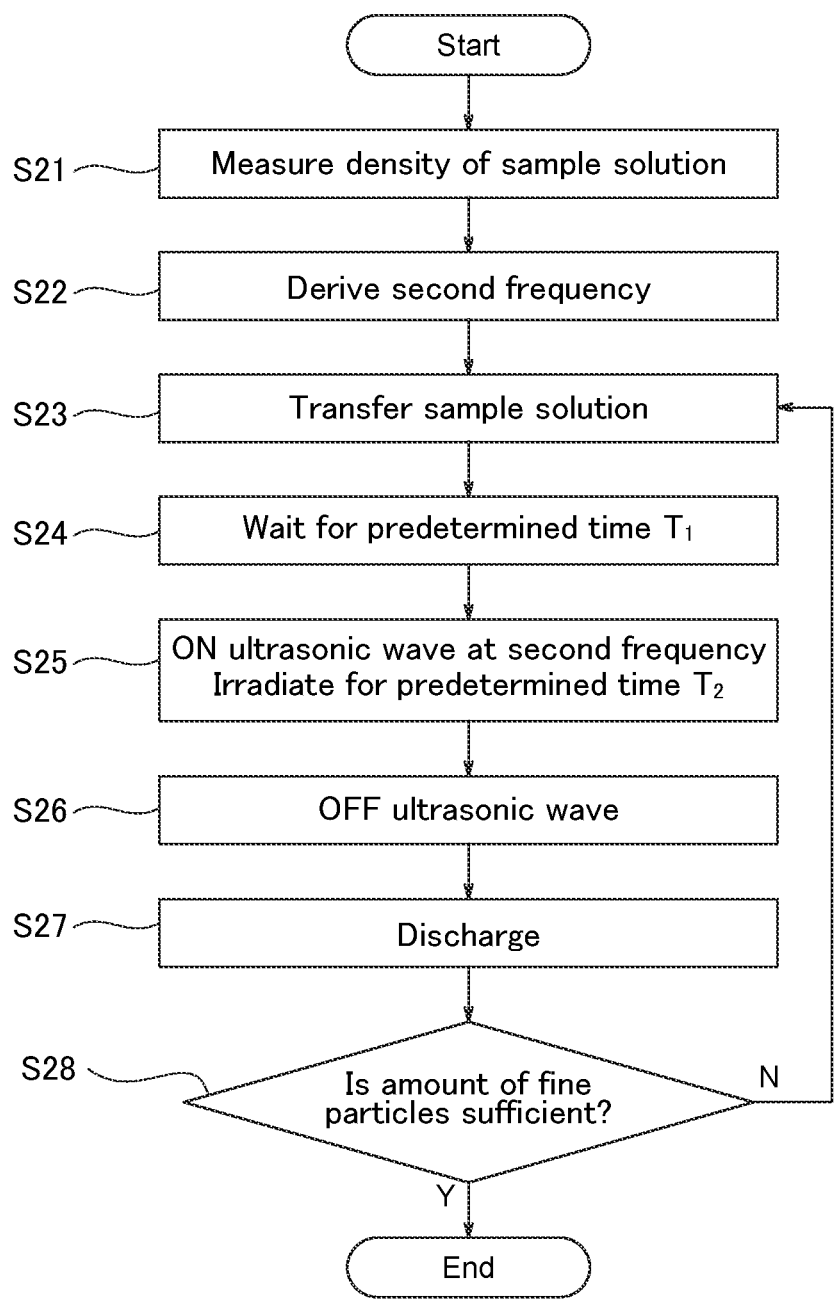
FIG. 7 is a flowchart of a particle concentration procedure by the particle recovery device according to the first exemplary embodiment of the present disclosure.

FIG. 7 is a flowchart of a particle concentration procedure according to the first exemplary embodiment of the present disclosure, and a procedure of particle concentration treatment will be described with reference to FIG. 7.

First, as a first step S21, only the first pump 20 is driven in the state where the second pump 22 is stopped, whereby the sample solution 30 stored in the spitz tube 12 is caused to flow into the density measurement unit 60. Then, the density measurement unit 60 measures the density of the sample solution 30 and transmits the density measurement value of the sample solution 30 to the control unit 44.

Next, as a second step S22, the control unit 44 derives the second frequency for the sample solution 30 based on the density value of the sample solution 30 received from the density measurement unit 60 and the density versus frequency relationship stored in the storage unit 70.

Next, as a third step S23, only the first pump 20 is further driven, whereby the sample solution 30 is caused to flow into the flow path 50 in the flow cell 40.

Next, in a fourth step S24, after the sample solution 30 is caused to flow into the flow path 50, the first pump 20 is stopped, and waiting is performed only for the predetermined time T1 until the flow of the sample solution 30 in the flow path 50 does not flow.

Next, as a fifth step S25, the piezoelectric element 42 is vibrated by supplying the alternating-current voltage from the oscillator 16 to the piezoelectric element 42, and the sample solution 30 in the flow path 50 is irradiated with vibration (ultrasonic wave) of the second frequency derived in S22 for the predetermined time T2. The node N is generated on the central axis of the flow path 50, and the particles in the flow path 50 move to the position of the node N.

Next, a sixth step S26 is performed. Since S26 is the same as S14, the description thereof will be omitted.

Next, a seventh step S27 is performed. Since S27 is the same as S15, the description thereof will be omitted.

Next, as an eighth step S28, an amount of the concentrated solution discharged to the inner tube 58 is measured, and it is confirmed whether the amount of the concentrated solution suitable for the intended use has been obtained. At this time point, when a sufficient amount of the concentrated solution has not been obtained, the process returns to the third step S23, and when a sufficient amount of the concentrated solution has been obtained, the concentration procedure is terminated.

Operation and Advantageous Effects

By performing the particle concentration treatment by the above-described procedure, the following operations and effects are obtained.

First, in the particle recovery device 10 according to the first exemplary embodiment of the present disclosure, the frequency (second frequency) of the ultrasonic wave with which the flow path 50 is irradiated by the control unit 44 is derived from the density value of the sample solution 30 measured by the density measurement unit 60 and the density versus frequency relationship. The second frequency derived from the density value of the sample solution 30 and the density versus frequency relationship is presumed to be a frequency showing a high recovery rate. Then, the sample solution 30 in the flow path 50 is irradiated with the ultrasonic wave of the second frequency derived by the control unit 44 from the ultrasonic irradiation unit.

As a result, the particles dispersed in the sample solution 30 are focused at the position of the node N of the standing wave SW.

Here, when the plurality of sample solutions 30 are provided and the density of the sample solution 30 is different among the plurality of sample solutions 30, the frequency of the ultrasonic wave at which the particles in the sample solution 30 are efficiently recovered is different for each of the sample solutions 30.

However, in the particle recovery device 10 according to the first exemplary embodiment of the present disclosure, the density of the sample solution 30 is measured by the density measurement unit 60. Thus, the density is measured for each of the sample solutions 30, and the frequency of the ultrasonic wave at which the particles contained in the sample solution 30 are recovered well are obtained from the obtained density value of the sample solution 30 and the density versus frequency relationship stored in the storage unit 70.

As described above, in the particle recovery device 10 according to the first exemplary embodiment of the present disclosure, for the plurality of sample solutions 30, even when the density is different for each of the sample solutions 30 and the frequency at which the particles in the sample solution 30 are efficiently recovered is different, by determining the frequency of the ultrasonic wave with which the flow path is irradiated for each of the sample solutions 30, it is possible to apply the ultrasonic wave having the frequency at which the particles in the sample solution 30 can be efficiently recovered.

Therefore, even when the particles of the plurality of sample solutions 30 are measured by a series of operations, the particles can be concentrated, operation efficiency can be improved, and the recovery rate of the tangible component can be stabilized.

As described above, since the number of the nodes N of the standing wave SW at the optimal frequency is 1, the particles are concentrated at the radial center of the flow path 50, which is the position of the node N.

Here, a double tube including the outer tube 56 and the inner tube 58 disposed inside the outer tube 56 along the central axis of the outer tube 56 is connected to the discharge port 54 of the particle recovery device 10 according to an exemplary embodiment of the present disclosure, the outer tube 56 is disposed coaxially with the flow path 50, and the inner tube 58 is disposed on the central axis of the flow path 50.

Therefore, in the sample solution 30 filled in the flow path 50, the concentrated solution 34 easily flows to the inner tube 58, the low-concentration liquid 32 easily flows to the outer tube 56, and the concentration efficiency of the particles can be improved.

As described above, in the particle recovery device 10 according to the first exemplary embodiment of the present disclosure, the flow of the sample solution 30 stops in the flow path 50 after the sample solution 30 flows into the flow path 50, and vibration is applied to the sample solution 30 in a stored state, so that the sample solution 30 can be suppressed from flowing inside the flow path 50.

Therefore, when the sample solution 30 is discharged from the flow path 50, the flow of the sample solution 30 can be brought into a laminar flow state so that the concentrated solution 34 easily flows to the inner tube 58 and the low-concentration liquid 32 easily flows to the outer tube 56. As a result, the concentration efficiency of the particles can be improved.

Modification

In the above description, the density measurement unit 60 and the storage unit 70 are the configurations of the particle recovery device 10; however, the configuration of the particle recovery device 10 according to the first exemplary embodiment of the present disclosure is not limited thereto.

Figure 8:
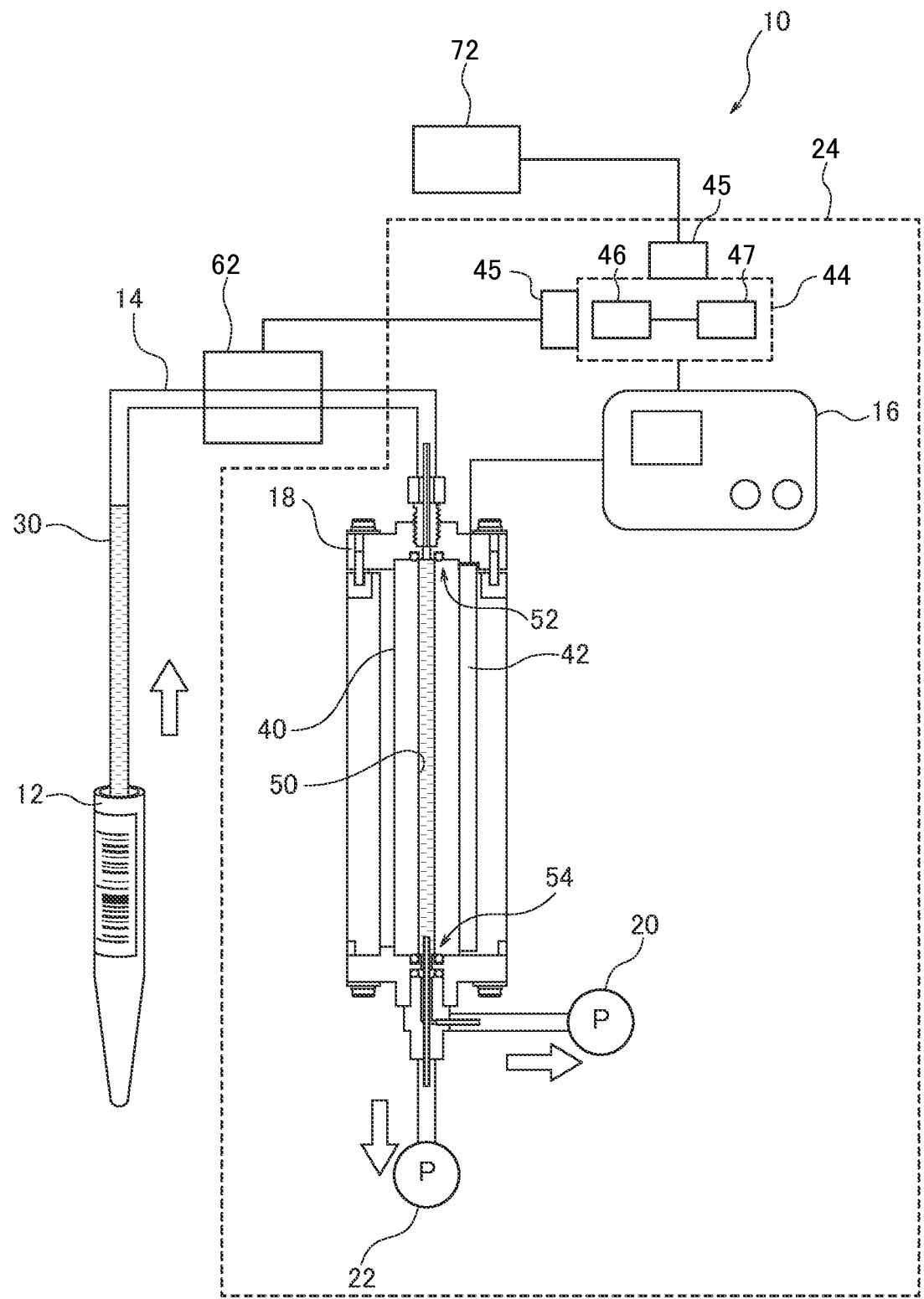
FIG. 8 is a schematic view of a configuration of a modification of the particle recovery device according to the first exemplary embodiment of the present disclosure.

For example, as shown in FIG. 8, the density measurement device 62 and the storage device 72 may be provided separately from a housing 24 that stores the supporting member 18, the oscillator 16, the first pump 20, the second pump 22, and the control unit 44. The density measurement device 62 and the storage device 72 are connected to the control unit 44. Also in this case, the introduction path 14 is connected to the spitz tube 12, and the sample solution 30 stored in the spitz tube 12 flows through the introduction path 14 and is introduced into the flow cell 40.

Then, the density measurement device 62 provided in the middle of the introduction path 14 transmits the density value of the sample solution 30 to the control unit 44 of the particle recovery device 10. The control unit 44 determines the frequency of the ultrasonic wave by receiving the density value of the sample solution 30 received from the density measurement device 62 and the density versus frequency relationship from the storage device 72.

Also in this case, the same effects as those of the particle recovery device 10 according to the first exemplary embodiment of the present disclosure can be obtained.

For example, not only the frequency may be determined according to the density of the sample solution 30 as described above, but also the amplitude of the ultrasonic wave to be applied in S25 and the irradiation time T2 of the ultrasonic wave may be determined according to the density of the sample solution 30.

Even when the sample solution 30 is irradiated with the ultrasonic wave of the second frequency, the recovery rate of the tangible component contained in the sample solution 30 having a high density is lower than the recovery rate of the tangible component contained in the sample solution 30 having a low density. Thus, the sample solution 30 having a high density is irradiated with the ultrasonic wave having an amplitude larger than the amplitude of the ultrasonic wave with which the sample solution 30 having a low density is irradiated, or the sample solution 30 having a high density is irradiated with the ultrasonic wave for a time longer than the time for irradiating the sample solution 30 having a low density with the ultrasonic wave. As a result, the particles of the sample solution 30 having different densities can be recovered at a stable recovery rate.

Figure 9:
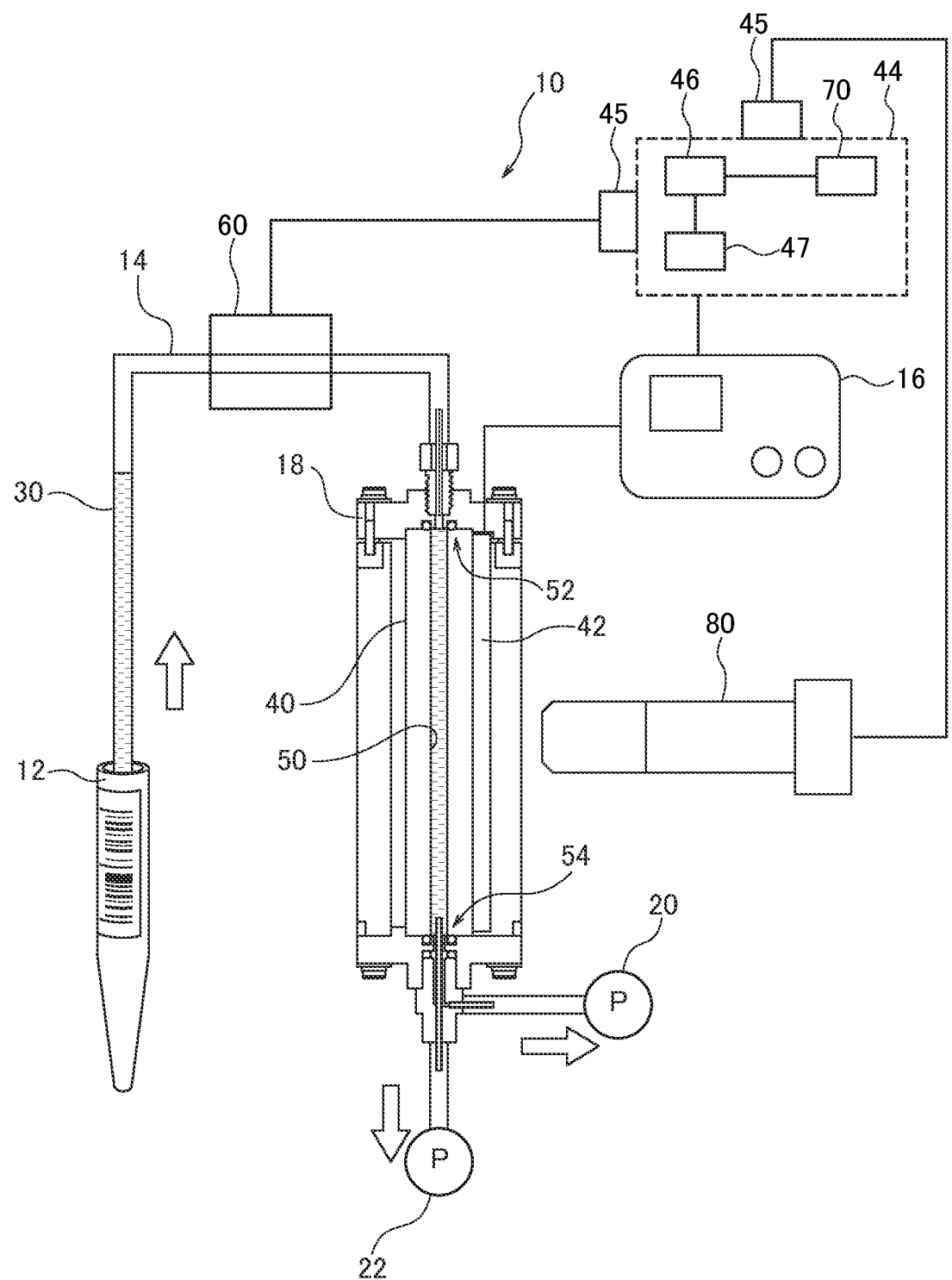
FIG. 9 is a schematic view of the configuration of the modification of the particle recovery device according to the first exemplary embodiment of the present disclosure.

As described above, since the flow cell 40 is formed of glass as an example, the tangible component contained in the sample solution 30 flowing in the flow path 50 are observed through the flow cell 40. From this, as shown in FIG. 9, the particle recovery device 10 according to the present disclosure may further include an image detector 80 that observes the inside of the flow path 50 at a position where the flow cell 40 is viewed from the side.

In this case, the image detector 80 acquires a state in which the particles are focused in the flow path 50 and transmits the state to the control unit 44. As a result, the control unit 44 can correct the frequency of the ultrasonic wave, the amplitude of the ultrasonic wave, or the predetermined time T2 in S25 of the concentration treatment procedure based on the state in which the particles are focused.

When the control unit 44 has an input unit to which the density of the sample solution 30 measured in advance is input, and the frequency is determined based on the input density value of the sample solution 30, the particle recovery device 10 may be a configuration that does not have the density measurement unit 60. The input unit corresponds to the density acquisition unit.

The input unit is, for example, a button, a terminal, or the like for an operator of the particle recovery device 10 to input the density to the control unit. For example, when the sample solution 30 is urine, a part of the urine of a subject collected in a urine collection cup is dispensed into the spitz tube 12, and a part of the urine is left in the urine collection cup. A creatinine concentration in the urine correlated with the density of urine is measured by immersing a creatinine test paper in the urine remaining in the urine collection cup. By inputting the measurement value of the creatinine concentration to the input unit, the density can be input to the control unit 44.

When the operator who operates the particle recovery device 10 directly determines the frequency corresponding to the density of the sample solution 30, the particle recovery device 10 may be a configuration that does not have the storage unit 70.

In the above description, the density measurement unit 60 measures the density of the sample solution 30 from the volume and weight of the sample solution 30; however, the present invention is not limited thereto, and a value having a known correlation with the density may be used. For example, the osmotic pressure, refractive index, electrical resistivity, the creatinine concentration, or the like of the sample solution 30 may be measured, and the obtained value may be used instead of the density in the above description.

By further providing pressurizing means, such as a liquid feeding pump, in the middle of the introduction path 14, the sample solution 30 in the flow path 50 may be pressurized in a state where the inflow of the sample solution 30 into the flow path 50 is completed.

In this case, since the sample solution 30 in the flow path 50 is pressurized by the pressurizing means during S25, it is possible to prevent cavitation from occurring in the sample solution 30 filled in the flow path 50. As a result, the concentration efficiency of the particles can be improved, and breakage of the particles can be prevented.

In the present exemplary embodiment, the piezoelectric element 42 is provided only on one side with respect to the flow direction of the flow cell 40; however, the present invention is not limited thereto. For example, the second piezoelectric element may be provided on the side opposite to the piezoelectric element 42 with respect to the flow direction of the flow cell 40. In this case, the ultrasonic wave generated from the second piezoelectric element and applied into the flow path 50 is an ultrasonic wave having a frequency and amplitude equal to those of the ultrasonic wave generated from the piezoelectric element 42 and applied into the flow path 50, and having a phase equal to that of the ultrasonic wave on the central axis of the flow path 50.

In the particle recovery device 10 described above, the diameter of the inner tube 58 is about half of that of the outer tube 56; however, an exemplary embodiment of the present disclosure is not limited thereto. For example, the recovery rate of the particles in the sample solution 30 may be appropriately set by variously preparing the ratio between the diameter of the inner tube 58 and the diameter of the outer tube 56.

Although the ratio of the discharge amount of the sample solution 30 according to the first pump 20 and the second pump 22 is equivalent to the ratio of the cross-sectional area of the inner tube 58 and the cross-sectional area of the outer tube 56, the ratio of the discharge amount of the sample solution 30 according to the first pump 20 and the second pump 22 in the particle recovery device 10 according to an exemplary embodiment of the present disclosure is not limited thereto. For example, the recovery rate of the particles in the sample solution 30 may be appropriately set by variously changing the ratio of the discharge amount of the sample solution 30 according to the first pump 20 and the second pump 22.

In the particle recovery device 10 described above, the predetermined number (the number of the nodes N obtained by the standing wave SW) is 1; however, the standing wave SW that can be taken by the particle recovery device 10 according to an exemplary embodiment of the present disclosure is not limited thereto. For example, as shown in the above-described expression (3), the frequency of the ultrasonic wave may be set such that n is an integer of 2 or more, and the number of the nodes N obtained by the standing wave SW is 2 or more (so-called high-order mode) to generate the standing wave SW. In this case, since the node N is also generated at a position deviated from the radial center of the flow path 50, the diameter of the inner tube 58 may be changed so as to correspond to the position of the node N. Instead of the double tube, the discharge port 54 may be a multiple tube in which a larger number of tubes are connected coaxially, and the inner tube 58 may be disposed at each position corresponding to the position where the node is generated.

Although the particle recovery device 10 according to an exemplary embodiment of the present disclosure can concentrate the particles in the sample solution 30, depending on the density, physical properties, and the like of the sample solution 30 and the particles, the particles may be concentrated not at the position of the node N but at the position of the antinode in the standing wave generated by the vibration of the piezoelectric element 42. In this case, the relationship among the first pump 20, the second pump 22, the outer tube 56, and the inner tube 58 described above may be reversed. That is, the particles can be concentrated when the inner tube 58 side is the low-concentration liquid 32 and the outer tube 56 side is the concentrated solution 34.

In the above description, the flow cell 40 has a substantially rectangular parallelepiped shape as an example; however, an exemplary embodiment of the present disclosure is not limited thereto. For example, the flow cell 40 may have a cylindrical shape or a regular polygonal columnar shape.

In the above description, the flow path 50 has a circular hole shape; however, an exemplary embodiment of the present disclosure is not limited thereto. For example, the flow path 50 may have a polygonal hole shape.

Second Exemplary Embodiment

Subsequently, a particle recovery device 10 according to a second exemplary embodiment of the present disclosure will be described. The same configuration and the same principle as those of the first exemplary embodiment will not be described.
(Configuration)

Figure 10:
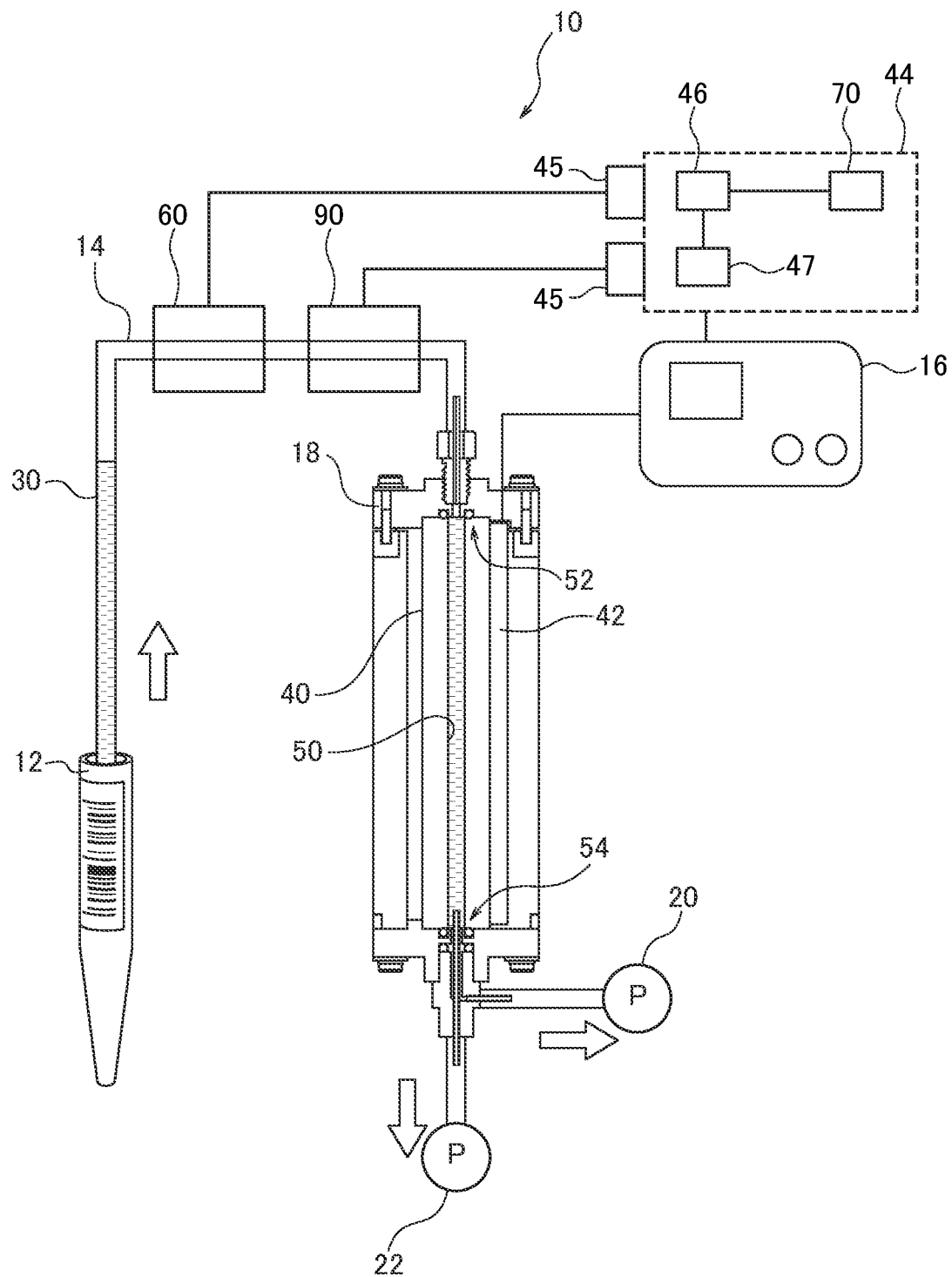
FIG. 10 is a schematic view of a configuration of a particle recovery device according to a second exemplary embodiment of the present disclosure.

FIG. 10 is a view showing a configuration of particle recovery according to the second exemplary embodiment of the present disclosure. As shown in FIG. 10, the particle recovery device 10 according to the second exemplary embodiment of the present disclosure is different from the particle recovery device 10 according to the first exemplary embodiment in the following points. That is, the particle recovery device 10 according to the second exemplary embodiment includes a component information acquisition unit 90 in the middle of an introduction path 14.

As an example, the component information acquisition unit 90 is provided in the middle of the introduction path 14, and measures the concentrations of a plurality of components contained in the sample solution 30 flowing through the introduction path 14 and flowing into the flow cell 40. Then, the component information acquisition unit 90 transmits a measurement value of the concentrations of the plurality of components of the sample solution 30 to a control unit 44. That is, the control unit 44 according to the second exemplary embodiment receives the density value of the sample solution 30 from a density measurement unit 60, and receives the measurement value of the concentrations of the plurality of components contained in the sample solution 30 from the component information acquisition unit 90.

The component measured by the component information acquisition unit 90 is a component having a significantly different concentration and contained in the sample solution 30 depending on an individual of the sample solution 30, and is a component that affects the density of the sample solution 30. The component measured by the component information acquisition unit 90 can be appropriately set according to the type of the sample solution 30. When the sample solution 30 is urine, the components measured by the component information acquisition unit 90 are, for example, glucose, urea, and albumin. As the component information acquisition unit 90, for example, a biosensor such as a glucose sensor can be used.

Then, the frequency of the alternating-current voltage supplied to the piezoelectric element by the oscillator 16 is determined based on the received density value of the sample solution 30, the received value of the concentrations of the plurality of components contained in the sample solution 30, and the correspondence relationship between the density and the frequency for each component measured by the component information acquisition unit and stored in the storage unit 70.

Other configurations are the same as those of the particle recovery device 10 according to the first exemplary embodiment.
(Determination of Optimal Frequency)

Also in the particle recovery device 10 according to the second exemplary embodiment, similarly to the particle recovery device 10 according to the first exemplary embodiment, the first frequency is obtained by the procedure shown in FIG. 5.

First, the density of the sample solution 30 and the concentrations of the plurality of components contained in the sample solution 30 are measured, and the correspondence relationship between the density of the sample solution 30 and the first frequency obtained as shown in FIG. 13 to be described later by the procedure for determining the first frequency according to the first exemplary embodiment is stored in the storage unit 70 as a "density versus frequency relationship" according to the second exemplary embodiment of the present disclosure.

In addition, in the procedure for measuring the frequency of the ultrasonic wave with which the sample solution 30 is irradiated according to the second exemplary embodiment, the measurement of the first frequency similarly showing the high recovery rate is performed on the plurality of sample solutions 30 containing the respective components measured by the component information acquisition unit 90 at the highest concentration.

Then, the correspondence relationship between the density of the sample solution 30 and the first frequency is stored in the storage unit 70 for each type of component contained in the sample solution 30 at the highest concentration.

Then, the optimal frequency according to the second exemplary embodiment is determined by deriving a second frequency from the density versus frequency relationship created using the sample containing the component contained at the highest concentration in the sample solution 30, the measurement value of the density of the sample solution 30, and the measurement values of the concentrations of the plurality of components.
(Procedure of Particle Concentration Treatment)

Subsequently, a particle concentration method according to the second exemplary embodiment of the present disclosure will be described with appropriate reference to FIG. 11.

Figure 11:
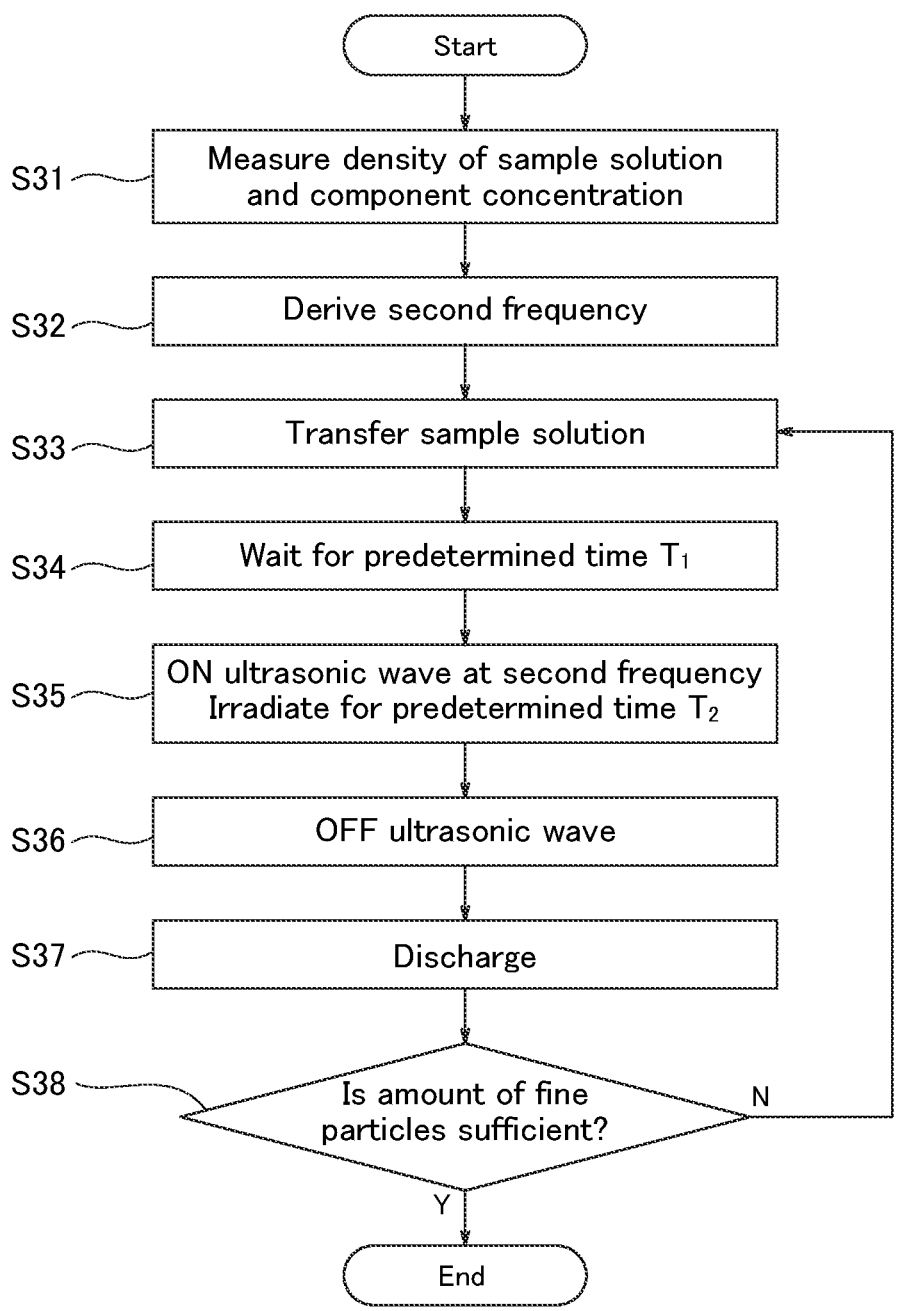
FIG. 11 is a flowchart of the particle concentration procedure by the particle recovery device according to the second exemplary embodiment of the present disclosure.

FIG. 11 is a flowchart of a particle concentration procedure according to the second exemplary embodiment of the present disclosure, and a procedure of particle concentration treatment will be described with reference to FIG. 11.

First, as a first step S31, only a first pump 20 is driven in the state where a second pump 22 is stopped, whereby the sample solution 30 stored in a spitz tube 12 is caused to flow into the density measurement unit 60 and the component information acquisition unit 90. Then, the density measurement unit 60 transmits the density value of the sample solution 30 to the control unit 44, and the component information acquisition unit 90 transmits the concentrations of the plurality of components contained in the sample solution 30 to the control unit 44.

Next, as a second step S32, the control unit 44 derives the second frequency for the sample solution 30 based on the density value of the sample solution 30 received from the density measurement unit 60 and the density versus frequency relationship stored in the storage unit 70.

The component contained in the sample solution 30 at the highest concentration is selected from among the components contained in the sample solution 30 based on the concentrations received from the component information acquisition unit 90, and the density versus frequency relationship stored in the storage unit 70, which is created using the sample solution 30 containing the same component as the selected component, is selected based on the selected component. Then, the second frequency is obtained based on the selected density versus frequency relationship and the value of the density of the sample solution 30, and the frequency (second frequency) of the ultrasonic wave with which the sample solution 30 is irradiated is determined.

Alternatively, the second frequency for each component is obtained from the "density versus frequency relationship" for each component stored in the storage unit 70 and the density value of the sample solution 30. The second frequency weighted by the concentration of each component can be obtained by multiplying the obtained second frequency for each component by a ratio of the measured concentration of each component, and the frequency of the ultrasonic wave with which the sample solution 30 is irradiated can be determined.

In the particle concentration procedure according to the second exemplary embodiment, S33 to S38 are the same as S23 to S28 in the particle concentration procedure according to the first exemplary embodiment.

Operation and Advantageous Effects

By performing the particle concentration treatment by the above-described procedure, the following operations and effects are obtained.

First, when the plurality of sample solutions 30 are provided and liquid properties such as the density and viscosity of the sample solution 30 are different among the plurality of sample solutions 30, the frequency of the ultrasonic wave at which the particles in the sample solution 30 can be efficiently recovered is different for each of the sample solutions 30. Specifically, the frequency at which particles of a sample having a high density can be recovered well tends to be higher than the frequency at which particles of a sample having a low density can be recovered well. However, when the concentration of each component contained in the sample solution 30 is different even in the sample solution 30 having the same density, the frequency of the ultrasonic wave at which the particles in the sample solution 30 can be efficiently recovered also slightly changes.

Here, since the particle recovery device 10 according to the second exemplary embodiment of the present disclosure further includes the component information acquisition unit 90 as compared with the particle recovery device 10 according to the first exemplary embodiment, the concentrations of the plurality of components of the sample solution 30 can be acquired.

Therefore, in the particle recovery device 10 according to the second exemplary embodiment of the present disclosure, the concentrations of the plurality of components contained in the sample solution 30 is measured, the second frequency is derived from the density versus frequency relationship created using the sample containing the measured component, the measurement value of the density of the sample solution 30, and the measured concentrations of the plurality of components, and the sample solution 30 is irradiated with the ultrasonic wave of the second frequency. Thus, the frequency of the ultrasonic wave with which the sample solution 30 is irradiated can be determined.

As a result, in the particle recovery device 10 according to the second exemplary embodiment of the present disclosure, it is possible to derive the optimal frequency that generates a stationary wave more accurately than the particle recovery device 10 according to the first exemplary embodiment of the present disclosure, and to recover the particles contained in the sample solution 30.

Other operation and advantageous effects are the same as those of the particle recovery device 10 according to the first exemplary embodiment.

Modification

In the above description, the particle recovery device 10 according to the second exemplary embodiment may further perform the following control.

In the particle recovery device 10 according to the second exemplary embodiment, the amplitude of the ultrasonic wave with which the sample solution 30 is irradiated may be adjusted according to the concentrations of the plurality of components measured by the component information acquisition unit 90. For example, when the amplitude of the ultrasonic wave with which the sample solution 30 is irradiated is reduced, it is possible to suppress the occurrence of the cavitation in the flow path and prevent the breakage of the particles. When the amplitude of the ultrasonic wave with which the sample solution 30 is irradiated is increased, the pressure due to the stationary wave generated in the flow path increases, so that the focusing of the particles can be accelerated.

For example, a predetermined time T2 for irradiating the sample solution 30 with the ultrasonic wave may be adjusted according to the type of the component measured at the highest concentration among the components measured by the component information acquisition unit 90. When the predetermined time T2 for irradiating the sample solution 30 with the ultrasonic wave is increased, the time during which the particles in the sample solution 30 are focused increases, so that the recovery rate can be improved. When the predetermined time T2 for irradiating the sample solution 30 with the ultrasonic wave is reduced, a time related to particle recovery operation is reduced, so that efficiency of particle recovery processing can be improved.

The control unit 44 has an input unit to which the concentrations of the plurality of components of the sample solution 30 measured in advance is input, and the control unit 44 can determine the frequency based on the input value of the concentrations of the plurality of components of the sample solution 30. In this case, the particle recovery device 10 may be a configuration that does not include the component information acquisition unit 90. The concentrations of the plurality of components contained in the sample solution 30 can be measured using, for example, a urine test paper.

When the operator who operates the particle recovery device 10 based on the concentrations of the plurality of components of the sample solution 30 directly determines the frequency of the ultrasonic wave with which the sample solution 30 is irradiated, the particle recovery device 10 may be a configuration that does not have the storage unit 70.

The modification of the particle recovery device 10 according to the first exemplary embodiment of the present disclosure can also be applied to the particle recovery device 10 according to the second exemplary embodiment of the present disclosure.

EXAMPLE

Next, the effects of the first exemplary embodiment of the present disclosure were verified from the following various experimental results. In the flow cell 40 used in the experiment, the longitudinal direction was 100 mm, a long side in the lateral direction (radial direction) was 16.9 mm, a short side in the lateral direction was 10 mm, and the diameter of the flow path 50 was 2.6 mm. The piezoelectric element 42 was disposed on one surface along the longitudinal direction on the short side in the lateral direction of the flow cell 40.

As the sample solution 30 of Sample 8, human epithelial cells which were tangible components were added as particles to urine prepared by mixing a plurality of urine of healthy persons. The density of the sample solution 30 of Sample 8 was 1.02 g/cm³. As Samples 5, 6, and 7, those described above were used. The contents of the description of Sample 8 are summarized in Table 2.

TABLE 2

| Sample No. | Tangible component | Density (g/cm³) | Type of sample solution |
|---|---|---|---|
| Sample 8 | Epithelial cell | 1.02 | Urine |

Experiment 1

As Experiment 1, the first frequency of each sample was measured at intervals of 0.5 kHz using the sample solutions 30 of Samples 1 to 7, and the effect of the particle recovery method according to the first exemplary embodiment of the present disclosure was confirmed.

Figure 12:
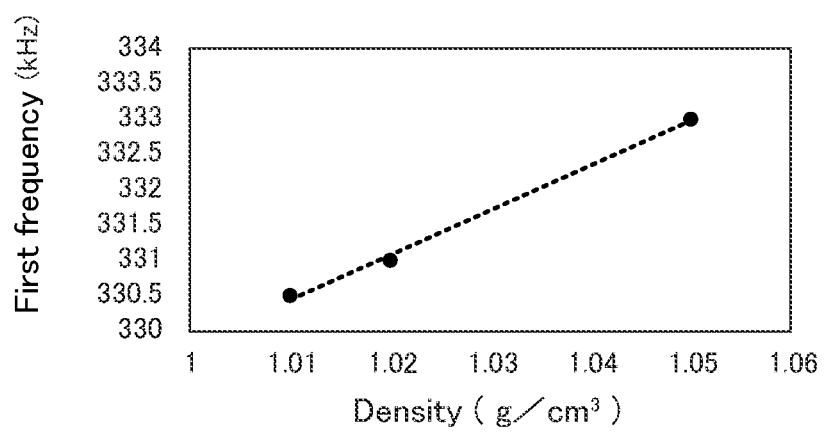
FIG. 12 is a graph showing a change in an optimal frequency due to a difference in density of a liquid sample using the particle recovery device according to the first exemplary embodiment of the present disclosure.

FIG. 12 is a view showing the results of measuring the first frequency at intervals of 0.5 kHz in each of the sample solutions 30 of Samples 1 to 7 by the procedure shown in FIG. 5, and using the median of the first frequency for each density (1.01 g/cm³, 1.02 g/cm³, and 1.05 g/cm³) from the obtained results.

More specifically, as shown in FIG. 6, Sample 1 having a density of 1.01 g/cm³ was irradiated with the ultrasonic waves of 330 kHz, 330.5 kHz, and 331 kHz to measure the recovery rate of the tangible components contained in Sample 1. As a result, the highest recovery rate was shown at 330.5 kHz. Thus, the first frequency of the sample solution 30 having a density of 1.01 g/cm³ was set to 330.5 kHz, and plotted in FIG. 12.

Samples 2 to 4 having a density of 1.02 g/cm³ were irradiated with the ultrasonic waves of 330.5 kHz, 331 kHz, and 331.5 kHz, and the recovery rate of the tangible components contained in Samples 2 to 4 was measured. The highest recovery rate was shown at 331 kHz in any of the sample solutions 30 of Samples 2 to 4. Thus, the first frequency of the sample solution 30 having a density of 1.02 g/cm³ was set to 331 kHz, and plotted in FIG. 12.

Samples 5 and 7 having a density of 1.05 g/cm³ were irradiated with the ultrasonic waves of 332.5 kHz, 333 kHz, and 333.5 kHz to measure the recovery rate of the tangible components contained in Samples 5 and 7.

For Sample 6 having a density of 1.05 g/cm³, the recovery rate of the tangible component was measured when the ultrasonic waves of 334 kHz and 334.5 kHz were further applied. The highest recovery rate was shown at 333 kHz for Sample 5, 334 kHz for Sample 6, and 332.5 kHz for Sample 7. 333 kHz which was the median of the frequency showing the highest recovery rate in Samples 5, 6, and 7 was plotted as the first frequency of the sample solution 30 having a density of 1.05 g/cm³ in FIG. 12.

In this experiment, the median obtained by measuring the first frequency of each of the plurality of sample solutions 30 having a density of 1.02 g/cm³ and having different components contained in the sample solution 30 is 1.02 g/cm³ and is used as the first frequency of the sample solution 30; however, an averaged sample solution obtained by mixing the plurality of sample solutions 30 having a density of 1.02 g/cm³ is prepared, and the first frequency of the averaged sample solution can be used as the first frequency of the sample solution 30 having a density of 1.02 g/cm³. The first frequency of the sample solution 30 having a density of 1.05 g/cm³ can also be determined in the same manner.

From FIG. 12, it can be seen that the optimal frequency increases as the density increases at each plot point. That is, from FIG. 12, it can be seen that the optimal frequency changes depending on the difference in density of the sample solution 30.

As shown in FIG. 12, the correspondence relationship between the density and the optimal frequency, that is, the density versus frequency relationship could be obtained in a linear function manner by interpolating between the plot points. In the example shown in FIG. 12, when the density was $\rho$ (g/cm³) and the frequency was f (kHz), f=63.462 $\rho$+266.35 was obtained as indicated by a dotted line in FIG. 12.

By storing the density versus frequency relationship thus obtained in the storage unit 70 of the particle recovery device 10 according to the first exemplary embodiment of the present disclosure, it can be said that the control unit 44 can determine the second frequency based on the density versus frequency relationship stored in the storage unit 70 even when the particles contained in the unknown sample solution 30 are focused and recovered. In this experiment, a correlation equation between the density and the first frequency is used as the density versus frequency relationship; however, a lookup table in which the density and the first frequency are compared may be used.

Figure 13A:
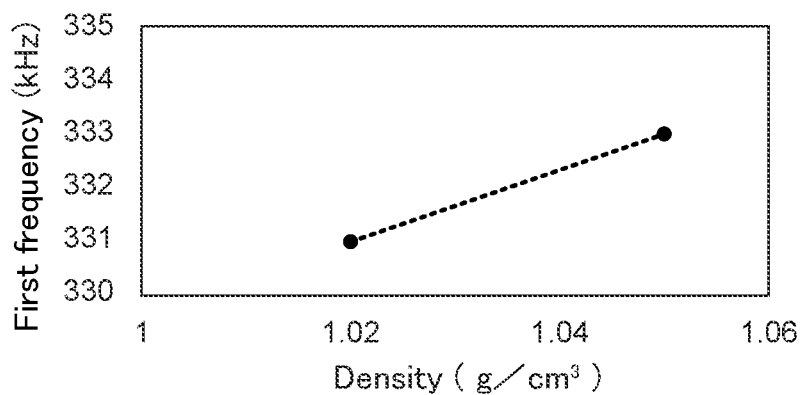
FIGS. 13A to 13C are graphs showing the change in the optimal frequency due to a difference in components of the liquid sample using the particle recovery device according to the first exemplary embodiment of the present disclosure.
Figure 13B:
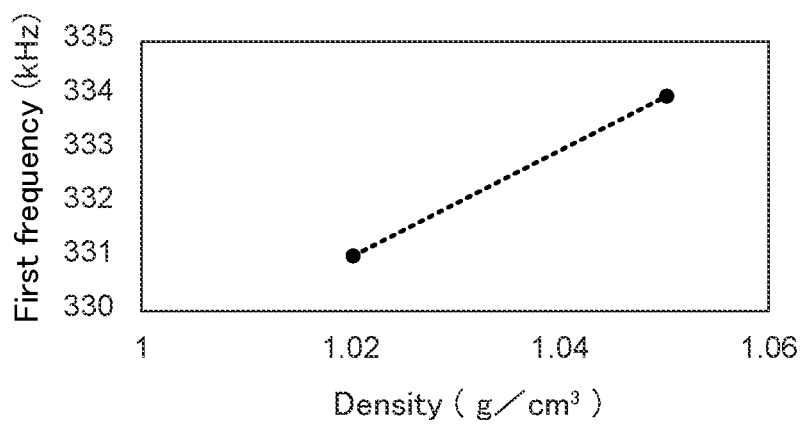
Figure 13C:
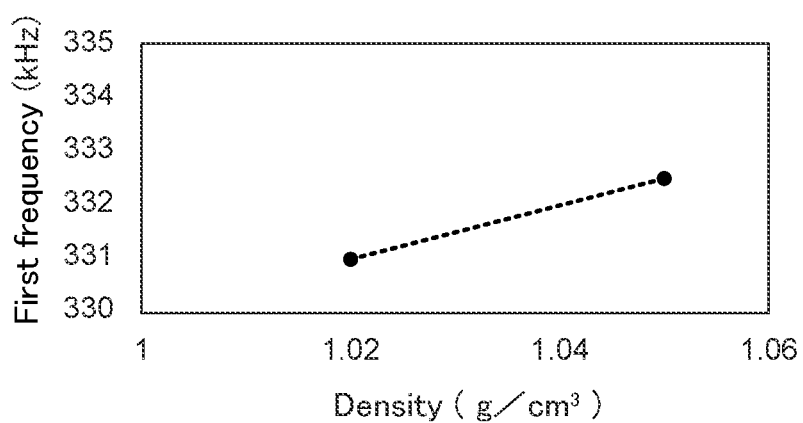

FIGS. 13A to 13C show the relationship between the density of the sample solution 30 and the first frequency for each of the added various components (glucose, urea, and albumin) in the sample solutions of Samples 2 to 7. That is, FIG. 13A shows the relationship between the density of the sample solutions 30 of Samples 2 and 5 in which the component contained in the sample solution at the highest concentration among the components contained in the sample solution is glucose and the first frequency. FIG. 13B shows the relationship between the density of the sample solutions 30 of Samples 3 and 6 in which the component contained in the sample solution at the highest concentration among the components contained in the sample solution is urea and the first frequency. FIG. 13C shows the relationship between the density of the sample solutions 30 of Samples 4 and 7 in which the component contained in the sample solution at the highest concentration among the components contained in the sample solution is albumin and the first frequency.

From FIGS. 13A to 13C, it can be seen that, as in FIG. 12, at each plot point, the density increases, and the first frequency also increases; however, a slope of the plot point, that is, the density versus frequency relationship is different for each of the various components. Therefore, from FIGS. 13A to 13C, it can be seen that the first frequency changes due to the difference in contained components even when the density of the sample solution 30 is about the same. In the examples shown in FIGS. 13A to 13C, when the frequency of the sample solution 30 to which glucose was added was $f_G$ (kHz), the frequency of the sample solution 30 to which urea was added was $f_B$ (kHz), and the frequency of the sample solution 30 to which albumin was added was $f_A$ (kHz), $f_G$=66.667 $\rho$+263 was obtained as indicated by a dotted line in FIG. 13A, $f_B$=100 $\rho$+229 was obtained as indicated by a dotted line in FIG. 13B, and $f_A$=50 $\rho$+280 was obtained as indicated by a dotted line in FIG. 13C.

As described above, the correspondence relationship between the density of the sample solution 30 and the first frequency is stored in advance in the storage unit 70 of the particle recovery device 10 according to the first exemplary embodiment of the present disclosure for each component contained in the sample solution 30 (for each component measured by the component information acquisition unit 90). Then, the correspondence relationship between the density and the first frequency for the component having the highest measured value among concentration measured values of the components detected by the component information acquisition unit 90 is read from the storage unit. The second frequency is derived using the read correspondence relationship and the density acquired by the density acquisition unit. As a result, even when the particles of the unknown sample solution 30 are focused and recovered, it can be said that the control unit 44 can determine the optimal frequency based on the density versus frequency relationship stored for each component in the storage unit 70.

As shown in FIGS. 13A to 13C, the inclination is different for each of the various components. Therefore, the control unit 44 may correct the frequency by weighting the concentrations of the plurality of components contained in the unknown sample solution 30 based on the density versus frequency relationship for each of the various components described above. As a result, the frequency of the ultrasonic wave that generates the standing wave SW with respect to the unknown sample solution 30 can be determined with higher accuracy.

Experiment 2

As Experiment 2, the recovery rate was measured using the sample solutions 30 of Samples 1 to 7, and the effect in the particle recovery method according to the first exemplary embodiment of the present disclosure was confirmed.

Figure 14:
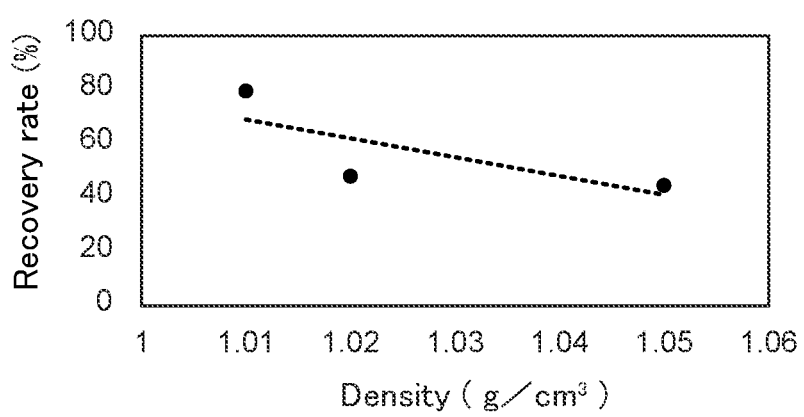
FIG. 14 is a graph showing the change in the recovery rate due to the difference in density of the liquid sample using the particle recovery device according to the first exemplary embodiment of the present disclosure.

FIG. 14 is a view showing the results of measuring the recovery rate by irradiating each of the sample solutions 30 of Samples 1 to 7 with the first frequency obtained in Experiment 1 described above in the procedure shown in FIG. 5 and using the median of the recovery rate for each density (1.01 g/cm$^3$, 1.02 g/cm$^3$, and 1.05 g/cm$^3$) from the obtained result. More specifically, the plot point of 1.01 g/cm$^3$ is the recovery rate of the sample solution 30 of Sample 1, the plot point of 1.02 g/cm$^3$ is the recovery rate of the sample solution 30 of Sample 2, and the plot point of 1.05 g/cm$^3$ is the recovery rate of the sample solution 30 of Sample 5.

From FIG. 14, it can be seen that the recovery rate decreases as the density increases at each plot point. That is, from FIG. 14, it can be seen that the recovery rate changes depending on the difference in density of the sample solution 30.

As shown in FIG. 14, the correspondence relationship between the density and the recovery rate could be obtained in a linear function manner by interpolating between the plot points. In the example shown in FIG. 14, when the density was $\rho$ (g/cm$^3$) and the recovery rate was C (%), C=−699.23 $\rho$+775.28 was obtained as indicated by a dotted line in FIG. 14.

By storing the correspondence relationship between the density of the sample solution 30 and the recovery rate thus obtained in the storage unit 70 of the particle recovery device 10 according to the first exemplary embodiment of the present disclosure, it can be said that the control unit 44 can determine the recovery rate based on the correspondence relationship stored in the storage unit 70 even when the particles contained in the unknown sample solution 30 are focused and recovered.

In the case of recovering the sample solution 30 in which the recovery rate decreases, that is, the particles of the sample solution 30 having a high density, measures such as increasing an amount of the sample solution 30 introduced and increasing the predetermined time T2 for applying the ultrasonic wave may be taken in order to compensate for the decreased recovery rate.

Figure 15A:
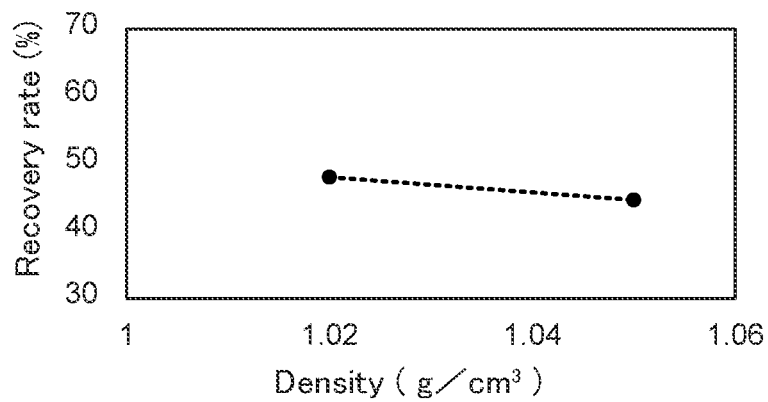
FIGS. 15A to 15C are graphs showing the change in the recovery rate due to the difference in components of the liquid sample using the particle recovery device according to the first exemplary embodiment of the present disclosure.
Figure 15B:
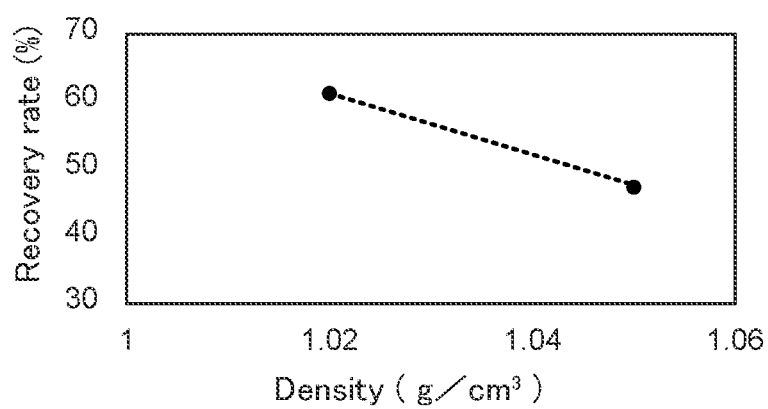
Figure 15C:
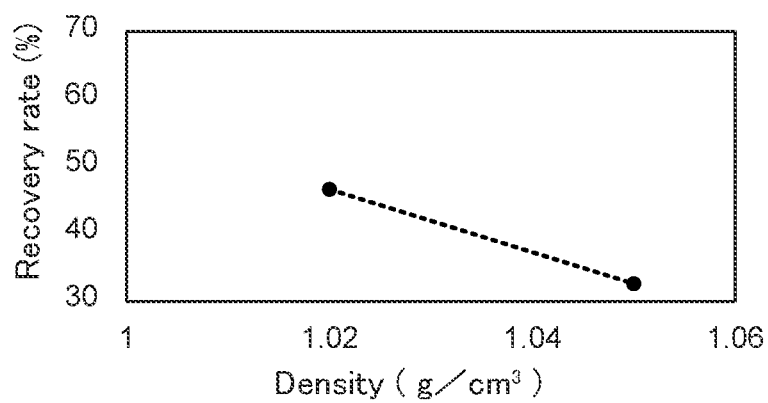

FIGS. 15A to 15C show the relationship between the density of the sample solution 30 and the recovery rate for each of the added various components (glucose, urea, and albumin) in the sample solutions of Samples 2 to 7. That is, FIG. 15A shows the results of Samples 2 and 5 with respect to the sample solution 30, FIG. 15B shows the results of Samples 3 and 6 with respect to the sample solution 30, and FIG. 15C shows the results of Samples 4 and 7 with respect to the sample solution 30.

From FIGS. 15A to 15C, it can be seen that, as in FIG. 14, at each plot point, the density increases, and the recovery rate decreases; however, the slope of the plot point, that is, the correspondence relationship between the density and the recovery rate is different for each of the various components. Therefore, from FIGS. 15A to 15C, it can be seen that the recovery rate changes due to the difference in components contained in the sample solution 30. In the examples shown in FIGS. 15A to 15C, when the recovery rate of the sample solution 30 to which glucose was added was $C_G$ (%), the recovery rate of the sample solution 30 to which urea was added was $C_B$ (%), and the recovery rate of the sample solution 30 to which albumin was added was $C_A$ (%), $C_G$=−113.33 $\rho$+163.6 was obtained as indicated by a dotted line in FIG. 15A, $C_B$=−453.33 $\rho$+523.6 was obtained as indicated by a dotted line in FIG. 15B, and $C_A$=−466.67 $\rho$+522.6 was obtained as indicated by a dotted line in FIG. 15C.

By storing the correspondence relationship between the density of the sample solution 30 and the recovery rate thus obtained in the storage unit 70 of the particle recovery device 10 according to the first exemplary embodiment of the present disclosure, it can be said that the control unit 44 can determine the recovery rate based on the correspondence relationship stored in the storage unit 70 even when the particles in the unknown sample solution 30 are focused and recovered.

As shown in FIGS. 15A to 15C, the slope is different for each of the various components. Therefore, the control unit 44 may estimate the recovery rate based on the concentrations of the plurality of components acquired by the component information acquisition unit 90, a density measured value of the sample solution 30 acquired by the density acquisition unit, and the above-described correspondence relationship between the density and the recovery rate. As a result, the above measures can be more reliably applied to the unknown sample solution 30, and the particles in the sample solution 30 can be recovered.

Experiment 3

As Experiment 3, an influence of the amplitude in the ultrasonic wave to be applied was measured using the sample solutions 30 of Samples 5 and 8, and the effect in the particle recovery method according to the first exemplary embodiment of the present disclosure was confirmed.

In Experiment 3, with respect to the sample solutions 30 of Samples 5 and 8, in the procedure shown in FIG. 5, the frequency of the ultrasonic wave to be applied was used as the optimal frequency obtained in Experiment 1 described above, and a change in focusing efficiency was confirmed by changing the amplitude of the ultrasonic wave. More specifically, the amplitude of the ultrasonic wave was controlled by changing the alternating-current voltage supplied from the oscillator 16 to the piezoelectric element 42 between 50 V and 80 V, and the focusing efficiency at each voltage value was measured.

Here, the focusing efficiency is derived by using the reciprocal of the time (focusing time) taken from the start of irradiating the flow cell 40 with the ultrasonic wave until the tangible components contained in the sample solutions 30 of Samples 5 and 8 filled in the flow path 50 are focused at the center inside the flow path 50. That is, it can be said that as the reciprocal of the focusing time is larger, concentration is performed in a shorter time, and therefore efficiency is higher.

Figure 16A:
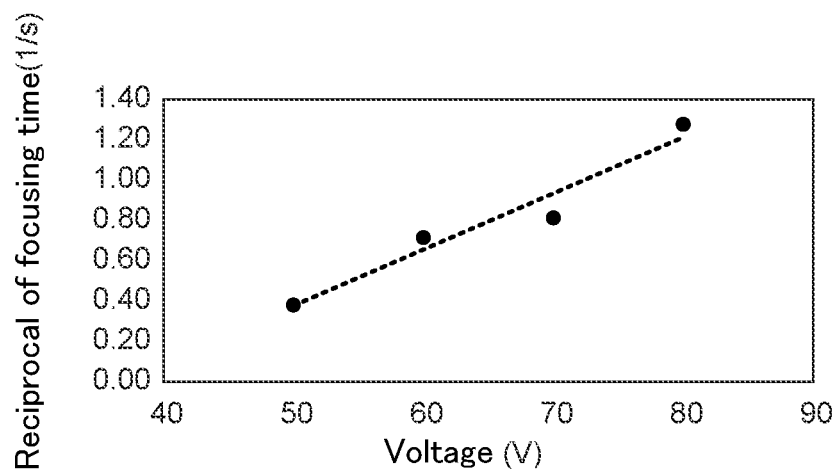
FIGS. 16A and 16B are graphs showing a change in reciprocal of a focusing time due to the difference in density of the liquid sample using the particle recovery device according to the first exemplary embodiment of the present disclosure and a difference in a voltage applied to a piezoelectric element.
Figure 16B:
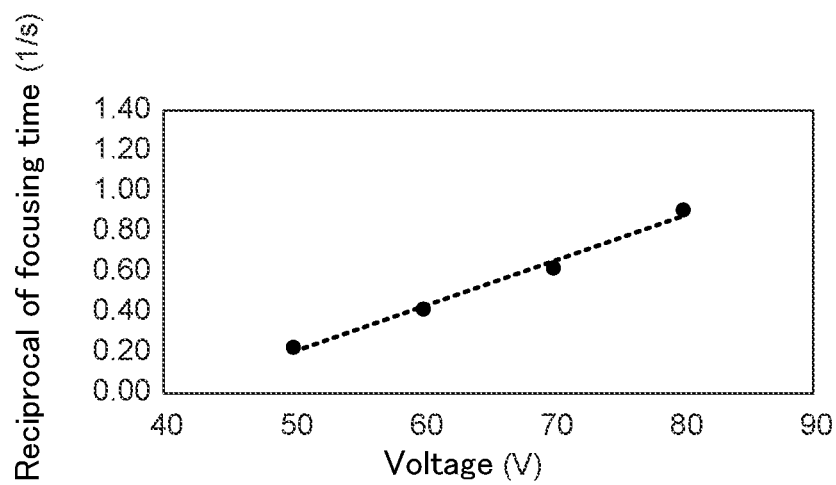

FIGS. 16A to 16B are views showing the result of the reciprocal of the obtained focusing time. FIG. 16A shows the result of Sample 8 with respect to the sample solution 30, and FIG. 16B shows the result of Sample 5 with respect to the sample solution 30.

From FIGS. 16A and 16B, at each plot point, the value of the reciprocal of the focusing time increases as the voltage supplied from the oscillator 16 to the piezoelectric element 42, that is, the amplitude of the ultrasonic wave increases; however, the reciprocal of the focusing time decreases when the density increases. Therefore, it can be seen that the focusing efficiency decreases when the density increases.

As shown in FIGS. 16A and 16B, the correspondence relationship between the voltage and the reciprocal of the focusing time could be obtained in a linear function manner by interpolating between the plot points. In the examples shown in FIGS. 16A and 16B, when the reciprocal of the focusing time of Sample 8 was $R_2$ (1/s), the reciprocal of the focusing time of Sample 5 was $R_6$ (1/s), and the voltage supplied to the piezoelectric element 42 was E (V), $R_2=0.0278$ E$-1.0143$ was obtained as indicated by a dotted line in FIG. 16A and $R_6=0.0225$ E$-0.9169$ was obtained as indicated by the dotted line in FIG. 15B, respectively.

By storing the correspondence relationship between the amplitude of the ultrasonic wave (the voltage value of the alternating-current voltage supplied to the piezoelectric element 42) and the focusing time with respect to the density of the sample solution 30 thus obtained in the storage unit 70 of the particle recovery device 10 according to the first exemplary embodiment of the present disclosure, the control unit 44 can adjust the focusing time based on the correspondence relationship stored in the storage unit 70 even when the particles contained in the unknown sample solution 30 are focused and recovered.

As can be seen from FIG. 16, when the particles of the sample solution 30 having a low density are recovered, in other words, when the particles of the sample solution 30 having high focusing efficiency are efficiently recovered, a measure for reducing the predetermined time T2 for applying the ultrasonic wave for focusing may be taken.

As a result, when the particles contained in the sample solution 30 having a low density are recovered, it can be said that the time for applying the ultrasonic wave can be shortened, and the efficiency of the operation of recovering the particles can be improved.

As can be seen from FIG. 16, when the particles of the sample solution 30 having a low density are recovered, in other words, when the particles of the sample solution 30 having high focusing efficiency are efficiently recovered, a measure for reducing the amplitude of the alternating-current voltage supplied from the oscillator 16 to the piezoelectric element 42, that is, the amplitude of the ultrasonic wave applied to the sample solution 30 may be taken.

As a result, when the particles contained in the sample solution 30 having a small density are recovered, it can be said that the generation of cavitation in the flow path 50 can be suppressed and the breakage of the particles can be prevented by reducing the amplitude of the ultrasonic wave to be applied.

Hereinabove, although the exemplary embodiments of the present disclosure have been described above with reference to the accompanying drawings, it is obvious that a person having ordinary knowledge in the technical field to which the present disclosure belongs can conceive of various modifications or applications within the scope of the technical idea described in the claims, and it is naturally understood that these also belong to the technical scope of the present disclosure.

INDUSTRIAL APPLICABILITY

The particle recovery device according to the present disclosure can be used, for example, in an analytical instrument for a liquid containing particles, and the particle recovery method according to the present disclosure can be used, for example, in an operation procedure of the analytical instrument for the liquid containing particles.

What is claimed is:

1. A tangible component recovery device for recovering tangible components contained in a liquid urine sample, the tangible component recovery device comprising:
   a flow cell having a flow path through which the liquid urine sample flows; and
   a controller,
   wherein the tangible component recovery device is configured to:
      using the controller, acquire a density of the liquid urine sample;
      recover tangible components from a predetermined location in the flow path;
      using the controller, determine a frequency of an ultrasonic wave that generates a standing wave in the flow path based on the density; and
      apply the ultrasonic wave of the determined frequency into the flow path,
   wherein the frequency is determined so that a node of the standing wave is formed at the predetermined location in the flow path, and the tangible component recovery device recovers the tangible components gathered by the standing wave.

2. The tangible component recovery device according to claim 1, wherein the density of the liquid urine sample is acquired from a density measurement device that is connected to the tangible component recovery device and measures the density of the liquid urine sample.

3. The tangible component recovery device according to claim 1, wherein acquiring the density of the liquid urine sample includes measuring the density of the liquid urine sample.

4. The tangible component recovery device according to claim 1, wherein the tangible component recovery device is configured to, using the controller:
   store a density versus frequency relationship, which is a correspondence relationship between the density of the liquid urine sample in the flow path and the frequency of the ultrasonic wave that generates the standing wave in the liquid urine sample, and determine the frequency of the ultrasonic wave based on a frequency derived from a value of the density of the liquid urine sample and the density versus frequency relationship.

5. The tangible component recovery device according to claim 4, wherein the tangible component recovery device is configured to:
acquire concentrations of a plurality of components contained in the liquid urine sample in the flow path;
store the density versus frequency relationship for each of the plurality of components; and
determine the frequency of the ultrasonic wave based on the concentrations of the plurality of components contained in the liquid urine sample, the density of the liquid urine sample, and the plurality of density versus frequency relationships.

6. The tangible component recovery device according to claim 5, wherein the tangible component recovery device is configured to, using the controller, adjust an amplitude of the ultrasonic wave based on the concentrations of the plurality of components and the value of the density of the liquid urine sample.

7. The tangible component recovery device according to claim 5, wherein the tangible component recovery device is configured to, using the controller, adjust a length of time for applying the ultrasonic wave based on the concentrations of the plurality of components and the value of the density of the liquid urine sample.

8. The tangible component recovery device according to claim 1, wherein the tangible component recovery device is configured to, using the controller, adjust an amplitude of the ultrasonic wave based on the density.

9. The tangible component recovery device according to claim 1, wherein the tangible component recovery device is configured to adjust a length of time for applying the ultrasonic wave based on the density.

10. The tangible component recovery device according to claim 1, wherein:
a direction in which the standing wave is generated is a direction orthogonal to a flow direction of the liquid urine sample in the flow path, and
the tangible component recovery device comprises a double tube having an inner tube and an outer tube having a same axial center on a downstream side in the flow direction.

11. The tangible component recovery device according to claim 10, wherein, in the double tube, a cross-sectional area of an inside of the inner tube is equal to or less than ¼ of a cross-sectional area of an inside of the outer tube.

12. The tangible component recovery device according to claim 1, wherein the tangible component recovery device is configured to pressurize the liquid urine sample filled in the flow path,
wherein the tangible component recovery device is configured to irradiate the ultrasonic wave in a state in which the liquid urine sample is pressurized inside the flow path.

13. The tangible component recovery device according to claim 1, wherein the tangible component recovery device is configured to generate the standing wave in a state in which the liquid urine sample is stored in the flow path.

14. The tangible component recovery device according to claim 1, wherein a number of nodes of the standing wave is 1.

15. A tangible component recovery method of recovering tangible components contained in a liquid urine sample, the tangible component recovery method comprising:
acquiring a density of the liquid urine sample;
determining a frequency of an ultrasonic wave, which generates a standing wave in a flow path through which the liquid urine sample flows, based on the density of the liquid urine sample;
irradiating an inside of the flow path with the ultrasonic wave; and
recovering tangible components focused in the flow path by the standing wave generated by the irradiation with the ultrasonic wave.

16. The tangible component recovery method according to claim 15, wherein concentrations of a plurality of components contained in the liquid urine sample are measured, and the frequency of the ultrasonic wave to be applied into the flow path is determined based on the concentrations of the plurality of components, the density of the liquid urine sample, and a correspondence relationship for each of the components between the density of the liquid urine sample and the frequency of the ultrasonic wave that generates a standing wave in the liquid urine sample.

17. The tangible component recovery method according to claim 16, wherein an amplitude of the ultrasonic wave is adjusted based on the concentrations of the plurality of components contained in the liquid urine sample and the density.

18. The tangible component recovery method according to claim 16, wherein a length of time for applying the ultrasonic wave is adjusted based on the concentrations of the plurality of components contained in the liquid urine sample and the density.

19. The tangible component recovery method according to claim 15, wherein the liquid urine sample is a body fluid recovered from a living body.

20. The tangible component recovery method according to claim 15, wherein a number of nodes of the standing wave is 1.

* * * * *